US006043275A

United States Patent [19]
Maruyama et al.

[11] Patent Number: 6,043,275
[45] Date of Patent: Mar. 28, 2000

[54] 3,7-DITHIAPROSTANOIC ACID DERIVATIVE

[75] Inventors: Toru Maruyama; Shuichi Ohuchida, both of Mishima-gun, Japan

[73] Assignee: Ono Pharmaceutical Co., Ltd., Osaka, Japan

[ * ] Notice: This patent is subject to a terminal disclaimer.

[21] Appl. No.: 09/288,307

[22] Filed: Apr. 8, 1999

[30] Foreign Application Priority Data

Apr. 16, 1998 [JP] Japan .................................. 10-122836

[51] Int. Cl.$^{7}$ ..................... C07C 405/00; A01K 31/5575

[52] U.S. Cl. ............................ 514/530; 514/573; 560/15; 560/121; 562/426; 562/503

[58] Field of Search ..................... 560/15, 121; 562/426, 562/503; 514/530, 573

[56] References Cited

U.S. PATENT DOCUMENTS 5,731,452 3/1998 Minoshima ............................ 556/427
5,892,099 4/1999 Maruyama .............................. 560/121

FOREIGN PATENT DOCUMENTS 57-108065 7/1982 Japan .
58-110562 7/1983 Japan .
58-148857 9/1983 Japan .

*Primary Examiner*—Robert Gerstl
*Attorney, Agent, or Firm*—Stevens, Davis, Miller & Moesher, L.L.P.

[57] ABSTRACT

A 3,7-dithiaprostanoic acid derivative of the formula (I)

(I)

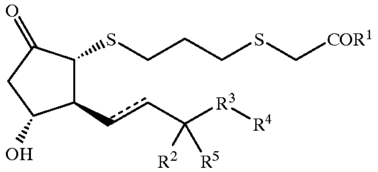

(wherein, $R^1$ is OH, C1~6 alkyloxy, $NR^6R^7$ ($R^6$, $R^7$ are H, C1~6 alkyl.); $R^2$ is H, OH; $R^3$ is single bond, C1~6 alkylene; $R^4$ is (i) C1~8 alkyl substituted by C1~6 alkyloxy, halogen etc., (ii) phenyloxy, C3~7 cycloalkyloxy, (iii) furyl, furyloxy, thienyl, thienyloxy, naphthyl, naphthyloxy, phthalanyl, phthalanyloxy, (iv) phenyl, phenyloxy, C3~7 cycloalkyl, C3~7 cycloalkyloxy substituted by C1~6 alkyl etc., (v) furyl, furyloxy, thienyl, thienyloxy, naphthyl, naphthyloxy, phthalanyl, phthalanyloxy substituted by C1~6 alkyl etc.; $R^5$ is H, C1~6 alkyl.) can bind $PGE_2$ receptor (particularly, EP4 subtype receptor) strongly. So, they are useful for the prevention and/or treatment of immunological diseases (autoimmune diseases, rejection after organ transplantation etc.), asthma, abnormal bone formation, neuronal cell death, liver damage, nephritis, hypertension, myocardiac ischemia and sleeping disorder etc.

16 Claims, No Drawings

3,7-DITHIAPROSTANOIC ACID DERIVATIVE

SUMMARY

The present invention relates to a 3,7-dithiaprostanoic acid derivative. More detail, it relates to (1) a 3,7-dithiaprostanoic acid derivative of the formula (I)

(I)

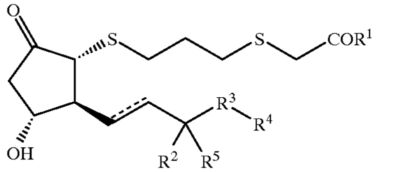

(wherein all the symbols are the same meaning as defined hereafter.), non-toxic salt thereof or, cyclodextrin clathrate thereof, (2) a process for the preparation thereof and (3) a pharmaceutical composition containing it as an active ingredient.

BACKGROUND

Prostaglandin $E_2$ (abbreviated as $PGE_2$) has been known as a metabolite in the arachidonate cascade. It has been known that $PGE_2$ possesses cyto-protective activity, uterine contractile activity, a pain-inducing effect, a promoting effect on digestive peristalsis, an awakening effect, a sleep-inducing effect (an awakening effect or a sleep-inducing effect may occur according to the action site of $PGE_2$.), a suppressive effect on gastric acid secretion, hypotensive activity and diuretic activity etc.

In the recent study, it was found that $PGE_2$ receptor was divided into some subtypes which possess different physical role from each other. At present, four receptor subtypes are known and they are called EP1, EP2, EP3 and EP4 (Negishi M. et al, J. Lipid Mediators Cell Signalling 12, 379–391 (1995)).

The present inventors have studied to find the compound which can bind to each receptor specifically, have found that the compound of the present invention of the formula (I) can bind to EP4 subtype receptor strongly, and then have achieved the present invention.

The compounds of the present invention of the formula (I) can bind EP4 subtype receptor strongly, so they are useful for the prevention and/or treatment of immunological diseases (autoimmune diseases such as ALS, multiple sclerosis, Sjoegren's syndrome, chronic rheumarthrosis and systemic lupus erythematosus etc. and rejection after organ transplantation etc.), asthma, abnormal bone formation, neuronal cell death, liver damage, nephritis, hypertension, myocardiac ischemia and sleeping disorder etc.

Among the compounds of the present invention of the formula (I), compounds which bind weakly to receptor subtypes except for EP4 receptor do not express other effects and therefore such compounds are expected to be an agent having less side effect.

On the other hand, a lot of prostaglandins in which carbon atom at 7th position in PG skeleton was replaced with sulfur atom have been known. For example, some patent application related to such compounds are listed as follows:

In the specification of Japanese Patent Application Kokai Sho 57–108065, it is disclosed that the following compounds are useful as platelet aggregation inhibitor.

I.e. 7-thiaprostaglandin derivative of the formula (A)

(A)

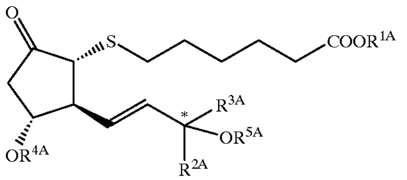

(wherein $R^{1A}$ is hydrogen, lower alkyl or pharmaceutically acceptable cation, $R^{2A}$ is hydrogen or methyl, $R^{3A}$ is C5~C7 alkyl or cycloalkyl, $R^{4A}$ and $R^{5A}$ are hydrogen or protecting group of hydroxy and symbol * means existence of an asymmetric carbon, in which its stereo configuration is α or β or mixture thereof in voluntary ratio.).

In the specification of Japanese Patent Application Kokai Sho 58-148857, it is disclosed that the following compounds are useful as platelet aggregation inhibitor.

I.e. 7-thiaprostaglandin derivative of the formula (B)

(B)

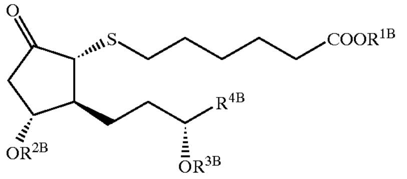

(wherein $R^{1B}$ is hydrogen or C1~C10 alkyl, 5~6-membered alicyclic ring or phenyl, $R^{2B}$ and $R^{3B}$ are, same or differently, hydrogen or tri (C1~C8)hydrocarbon-silyl or the group which are able to form acetal group taken together with oxygen atom in hydroxy and $R^{4B}$ is C3~C8 alkyl or 5~6-membered alicyclic ring.).

In the specification of Japanese Patent Application Kokai Sho 58-110562, it was disclosed that the following compounds are useful for control of vascular action.

I.e. 7-thiaprostaglandin derivative of the formula (C)

(C)

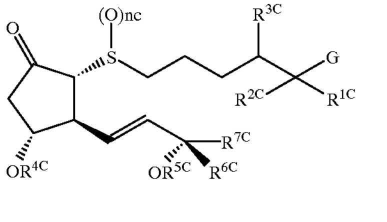

(wherein G is $—COOR^{8C}$, $—CONR^{9C}R^{10C}$ or $—CH^2OR^{11C}$, $R^{8C}$ is hydrogen, C1~C10 alkyl, substituted or unsubstituted phenyl, substituted or unsubstituted alicyclic ring, substituted or unsubstituted phenyl(C1~C3)alkyl or one equivalent cation, $R^{9C}$ and $R^{10C}$ are, the same or different, hydrogen, C1~C10 alkyl, substituted or unsubstituted C5~C8 alicyclic ring, substituted or unsubstituted phenyl, or substituted or unsubstituted phenyl(C1~C3 )alkyl, or $R^{9C}$, $R^{10C}$ and nitrogen atom which are connected by them taken together with may form 5~6-membered and substituted or unsubstituted ring which may contain another hetero atom(s), $R^{11C}$ is hydrogen, C1~C6 alkyl, substituted or unsubstituted C2~C7 acyl or tri(C1~C6 )hydrocarbon-silyl or the group which are able to form acetal group taken together with oxygen atom in hydroxy;

$R^{1C}$ and $R^{2C}$ are the same or different, hydrogen, halogen atom(s), methyl or ethyl, $R^{3C}$ is hydrogen, or $R^{3C}$ and $R^{1C}$ taken together with may form single bond;

$R^{4C}$ and $R^{5C}$ are the same or different, hydrogen or tri(C1~C6 )hydrocarbon-silyl or the group which are able to form acetal group taken together with oxygen atom in hydroxy, $R^{6C}$ is hydrogen, methyl or ethynyl which may be protected;

$R^{7C}$ is C3~C8 alkyl or substituted or unsubstituted 5~6-membered alicyclic ring and $n^C$ is 0 or 1.).

The above prior arts related to the compounds of the formula (A) and (B) show that these compounds in which carbon atom at 7th position of PG-skeleton are replaced with sulfur atom are useful as platelet aggregation inhibitor and that they are hard to be metabolized. Similarly, the above prior art related to the compounds of the formula (C) shows that these compounds are useful for control of vascular action.

DISCLOSURE OF THE INVENTION

The present invention relates to (1) a 3,7-dithiaprostanoic acid derivative of the formula (I)

(I)

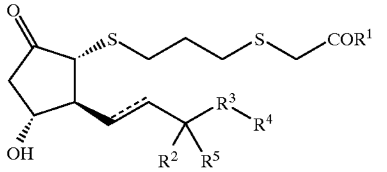

wherein $R^1$ is hydroxy, C1~6 alkyloxy or a group of the formula:

$NR^6R^7$ (in which $R^6$ and $R^7$ are independently hydrogen or C1~6 alkyl);

$R^2$ is hydrogen or hydroxy;

$R^3$ is single bond or C1~6 alkylene;

$R^4$ is (i) C1~8 alkyl, C2~8 alkenyl or C2~8 alkynyl substituted by one to three substituent(s) selected from the group consisting of C1~6 alkyloxy and halogen atom, (ii) phenyloxy or C3~7 cycloalkyloxy, (iii) furyl, furyloxy, thienyl, thienyloxy, naphthyl, naphthyloxy, phthalanyl or phthalanyloxy, (iv) phenyl, phenyloxy, C3~7 cycloalkyl or C3~7 cycloalkyloxy substituted by one to three substituent(s) selected from the group consisting of the following groups.

C1~6 alkyl,
C2~6 alkenyl,
C2~6 alkynyl,
C1~6 alkyloxy,
C1~6 alkyloxy-C1~6 alkyl,
C1~6 alkyloxy-C1~6 alkyloxy,
C2~6 alkenyloxy-C1~6 alkyl,
C1~6 alkyl substituted by 1 to 3 of hydroxy,
C1~6 alkyl substituted by 1 to 3 of halogen atom(s),
C1~6 alkylthio,
C1~6 alkylthio-C1~6 alkyl,
C1~6 alkylthio-C1~6 alkyloxy,
C2~6 alkenylthio-C1~6 alkyl,
C1~6 alkylsulfonyl,
halogen,
trihalomethyl,
cyano,
nitro,
amino,
hydroxy,
C3~7 cycloalkyl,
C3~7 cycloalkyloxy,
C3~7 cycloalkyl-C1~6 alkyl,
C3~7 cycloalkyloxy-C1~6 alkyl,
phenyl,
phenyloxy,
phenyl-C1~6 alkyl,
phenyl-C2~6 alkenyl,
phenyl-C2~6 alkynyl,
phenyloxy-C1~6 alkyl,
phenyloxy-C2~6 alkenyl,
phenyloxy-C2~6 alkynyl,
furyl,
furyloxy,
furyl-C1~6 alkyl,
furyloxy-C1~6 alkyl,
thienyl,
thienyloxy,
thienyl-C1~6 alkyl and
thienyloxy-C1~6 alkyl (the above mentioned phenyl, furyl, thienyl or cycloalkyl may be substituted by one to three substituent(s) selected from the group consisting of C1~6 alkyl, C1~6 alkyloxy, C1~6 alkyloxy-C1~6 alkyl, nitro, halogen, trihalomethyl, amino and hydroxy.), or (v) furyl, furyloxy, thienyl, thienyloxy, naphthyl, naphthyloxy, phthalanyl or phthalanyloxy substituted by one to three substituent(s) selected from the group consisting of the following groups:

C1~6 alkyl,
C2~6 alkenyl,
C2~6 alkynyl,
C1~6 alkyloxy,
C1~6 alkyloxy-C1~6 alkyl,
C1~6 alkyloxy-C1~6 alkyloxy,
C2~6 alkenyloxy-C1~6 alkyl,
C1~6 alkyl substituted by 1 to 3 of hydroxy,
C1~6 alkyl substituted by 1 to 3 of halogen atom(s),
C1~6 alkylthio,
C1~6 alkylthio-C1~6 alkyl,
C1~6 alkylthio-C1~6 alkyloxy,
C2~6 alkenylthio-C1~6 alkyl,
C1~6 alkylsulfonyl,
halogen,
trihalomethyl,
cyano, nitro,
amino,
hydroxy,
C3~7 cycloalkyl,
C3~7 cycloalkyloxy,
C3~7 cycloalkyl-C1~6 alkyl,
C3~7 cycloalkyloxy-C1~6 alkyl,
phenyl,
phenyloxy,
phenyl-C1~6 alkyl,
phenyl-C2~6 alkenyl,
phenyl-C2~6 alkynyl,
phenyloxy-C1~6 alkyl,
phenyloxy-C2~6 alkenyl,
phenyloxy-C2~6 alkynyl,
furyl,
furyloxy,
furyl-C1~6 alkyl,
furyloxy-C1~6 alkyl,
thienyl,
thienyloxy,
thienyl-C1~6 alkyl and
thienyloxy-C1~6 alkyl
(the above mentioned phenyl, furyl, thienyl or cycloalkyl may be substituted by one to three substituent(s) selected from the group consisting of C1~6 alkyl, C1~6 alkyloxy, C1~6 alkyloxy-C1~6 alkyl, nitro, halogen, trihalomethyl, amino and hydroxy.);

$R^5$ is hydrogen or C1~6 alkyl; and
the symbol

is double bond or single bond;
the formula including the 8-epi equilibrium compound;
with the proviso that when $R^2$ is hydrogen, C1~6 alkylene represented by $R^3$ may be substituted by a hydroxy group;
or a non-toxic salt thereof or a cyclodextrin clathrate thereof, (2) a process for the preparation thereof, and
(3) a pharmaceutical composition containing it as an active ingredient.

In the formula (I), C1~8 alkyl represented by $R^4$ means methyl, ethyl, propyl, butyl, pentyl, hexyl, heptyl, octyl and the isomer thereof.

In the formula (I), C1~6 alkyl in $R^1$ and $R^4$ and C1~6 alkyl represented by $R^5$, $R^6$, $R^7$ and $R^{10}$ means methyl, ethyl, propyl, butyl, pentyl, hexyl and the isomer thereof.

In the formula (I), C2~8 alkenyl represented by $R^4$ means vinyl, propenyl, butenyl, pentenyl, hexenyl, heptenyl, octenyl and the isomer thereof.

In the formula (I), C2~6 alkenyl in $R^4$ means vinyl, propenyl, butenyl, pentenyl, hexenyl and the isomer thereof.

In the formula (I), C2~8 alkynyl represented by $R^4$ means ethynyl, propynyl, butynyl, pentynyl, hexynyl, heptynyl, octynyl and the isomer thereof.

In the formula (I), C2~6 alkynyl in $R^4$ means ethynyl, propynyl, butynyl, pentynyl, hexynyl and the isomer thereof.

In the formula (I), C1~6 alkylene represented by $R^3$ means methylene, dimethylene, trimethylene, tetramethylene, pentamethylene, hexamethylene and the isomer thereof.

In the formula (I), C3~7 cycloalkyl in $R^4$ means cyclopropyl, cyclobutyl, cyclopentyl, cyclohexyl, cycloheptyl.

In the formula (I), halogen in $R^4$ and trihalomethyl means fluorine, chlorine, bromine and iodine.

In the present invention, the symbol

means double bond or single bond. Further, unless otherwise specified, in the present invention, the symbol

means that the substituent attached thereto is in front of the sheet, the symbol

means that the substituent attached thereto is behind the sheet and the symbol

 or 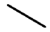

means that there is a mixture of substituents in front of and behind the sheet or that the substituent attached thereto may be in front of or behind the sheet as would be clear to the person skilled in the art.

Unless otherwise specified, all isomers are included in the present invention. For example, alkyl, alkenyl, alkynyl, alkylene group means straight-chain or branched-chain ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, I-isomer), polar compounds generated by chromatographic separation (more polar compound, less polar compound), equilibrium compounds, mixtures thereof at voluntary ratios and racemic mixtures are also included in the present invention.

Among the compounds wherein $R^2$ is hydroxy in the present invention, α-configuration, i.e. configuration in the natural type of prostaglandin, is preferable.

In addition, the configuration of the 8th position in the compounds of the present invention is shown as α-configuration, but as is clearto the person skilled in the art, the 8α-compounds are in equilibrium with the 8β-compounds (8-epi compounds). Therefore, the compounds of the formula (I) include mixtures of 8α-compounds and isomeric 8β-compounds.

Among the compounds of the present invention of the formula (I), the compounds described in the Examples and Reference Examples, the compounds shown in the following Tables 1~7 and the corresponding esters and amides are preferable. In each Table, Me means methyl.

TABLE 1
(1)
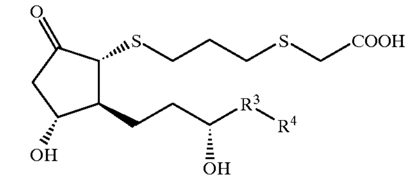
—$R^3$—$R^4$
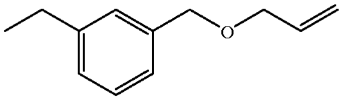
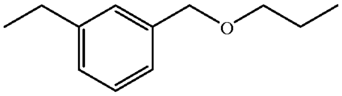
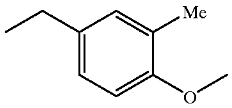
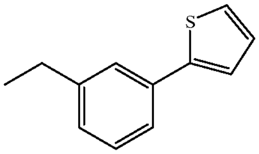
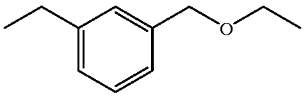
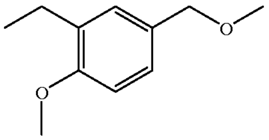
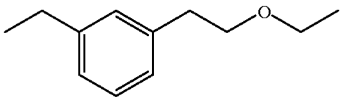
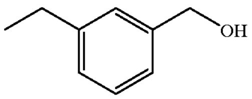
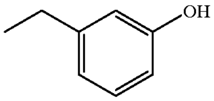
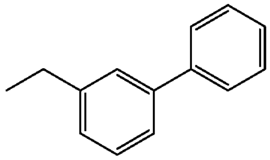
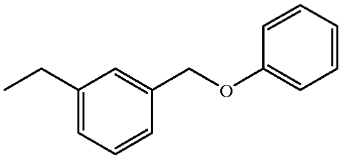
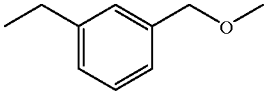
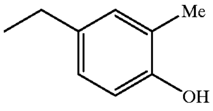
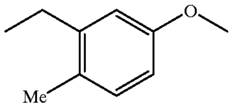
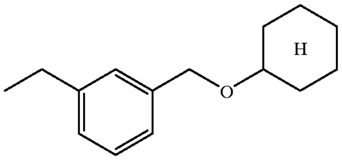
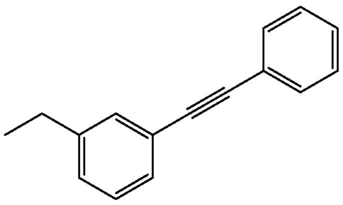
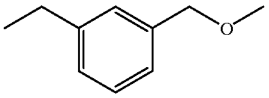
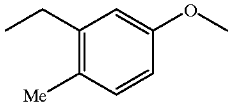
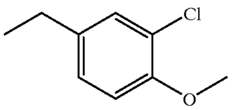
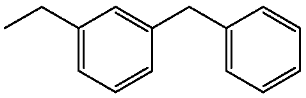
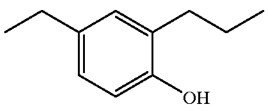
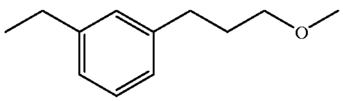

TABLE 1-continued
(1)
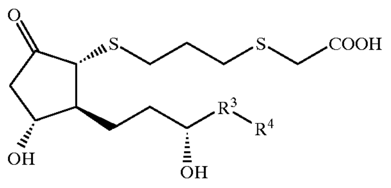
$—R^3—R^4$
| | |
|---|---|
| 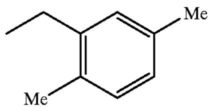 | 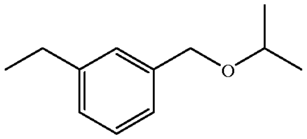 |
| 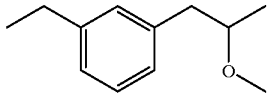 | 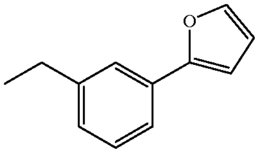 |
| 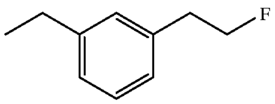 | 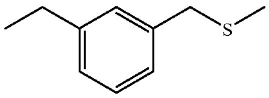 |
| 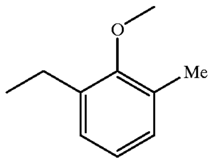 | 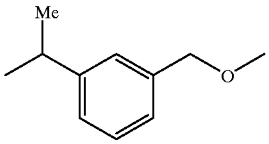 |
TABLE 2
(2)
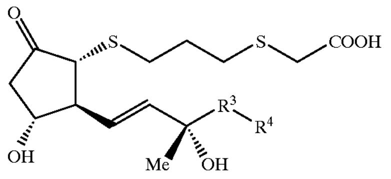
$—R^3—R^4$
| | | |
|---|---|---|
| 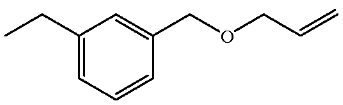 | 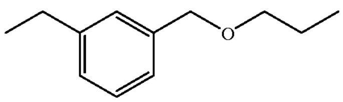 | 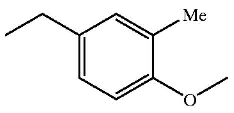 |
| 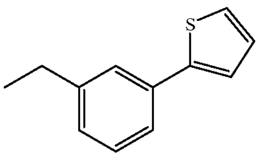 | 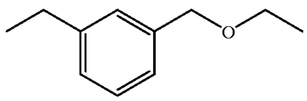 | 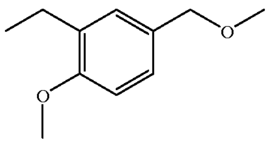 |

TABLE 2-continued
(2)
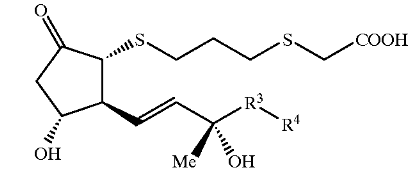
—$R^3$—$R^4$
| | | |
|---|---|---|
| 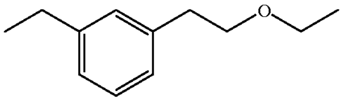 | 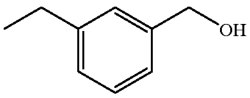 | 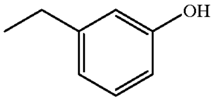 |
| 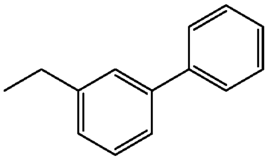 | 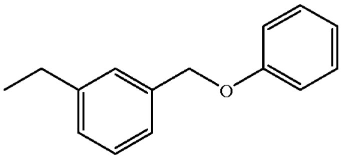 | 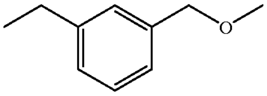 |
| 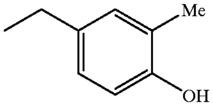 | 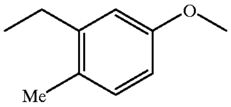 | 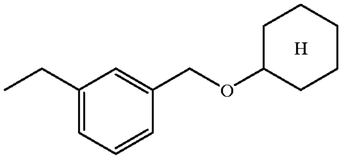 |
| 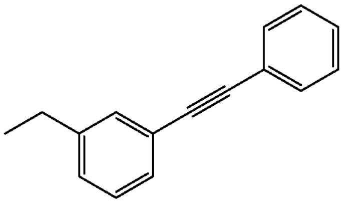 | 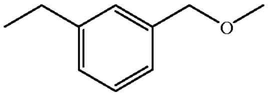 | 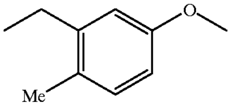 |
| 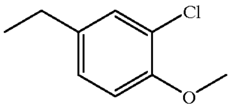 | 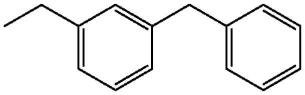 | |
| 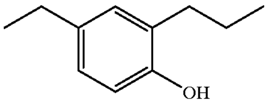 | 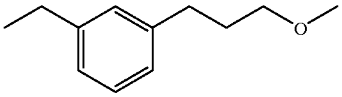 | |
| 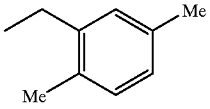 | 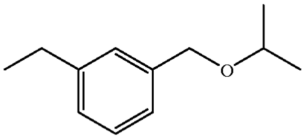 | |
| 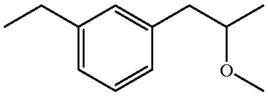 | 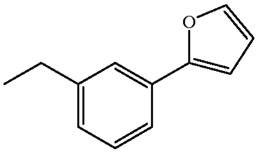 | |

TABLE 2-continued
| | |
|---|---|
| 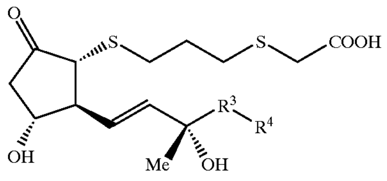 (2) | |
| $—R^3—R^4$ | |
| 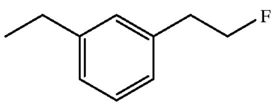 | 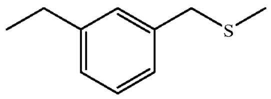 |
| 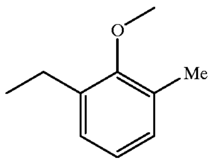 | |
TABLE 3
| | | |
|---|---|---|
| 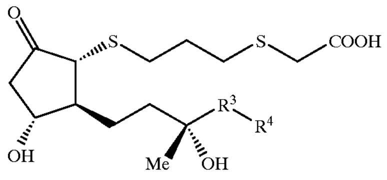 (3) | | |
| $—R^3—R^4$ | | |
| 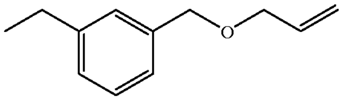 | 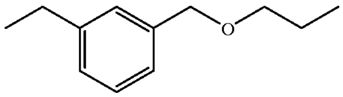 | 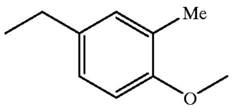 |
| 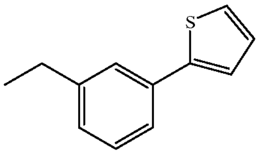 | 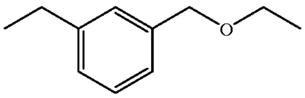 | 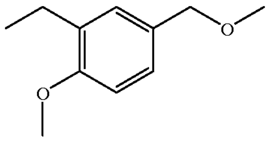 |
| 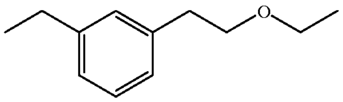 | 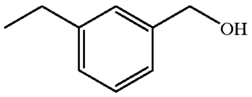 | 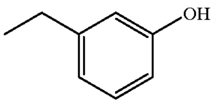 |
| 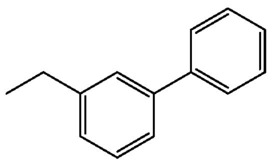 | 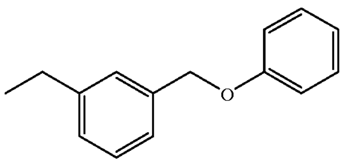 | 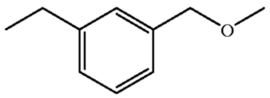 |

TABLE 3-continued
(3)
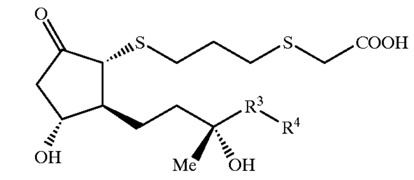
—$R^3$—$R^4$
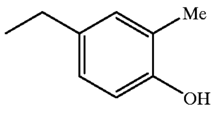 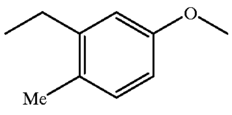 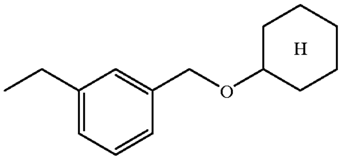
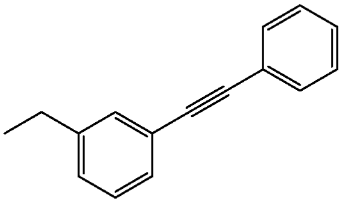 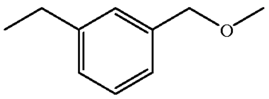 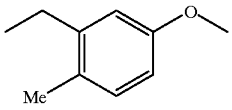
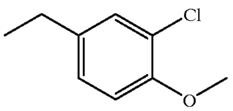 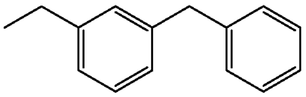
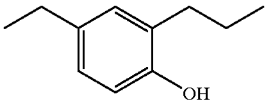 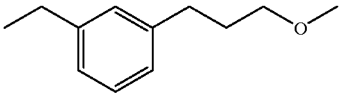
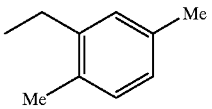 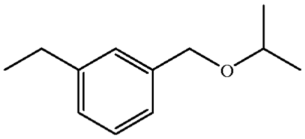
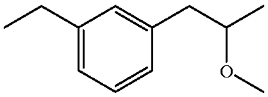 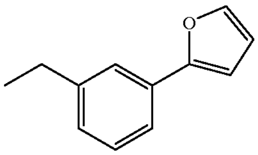
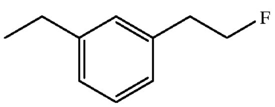 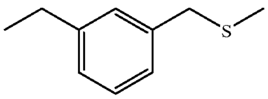
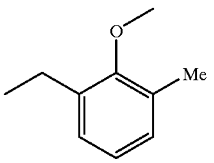

TABLE 4
(4)
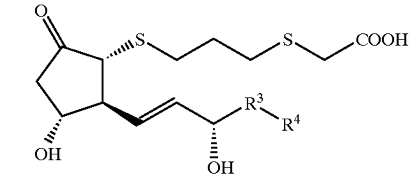
—$R^3$—$R^4$
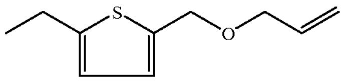
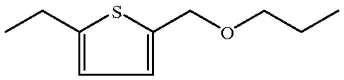
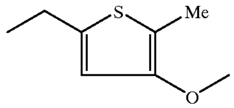
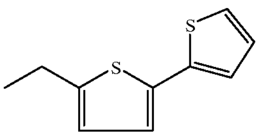
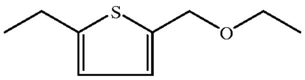
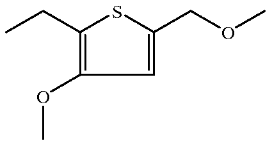
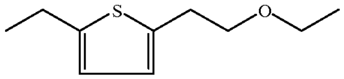
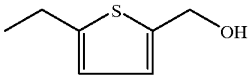
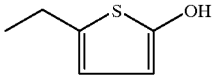
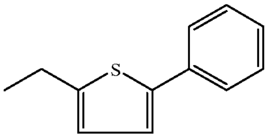
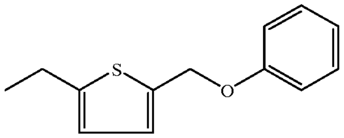
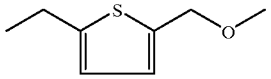
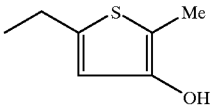
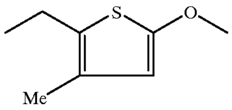
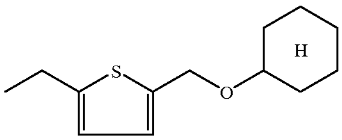
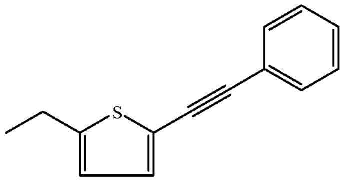
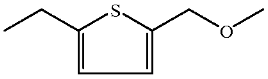
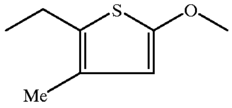
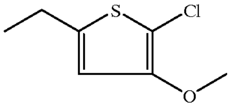
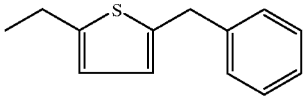
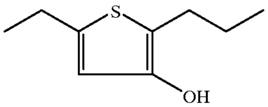
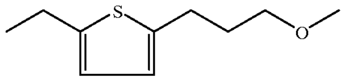
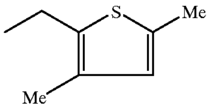
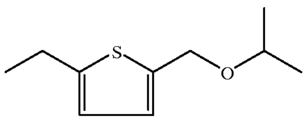

TABLE 4-continued
(4)
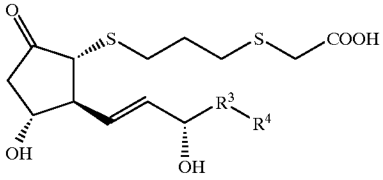
| —R³—R⁴ | |
|---|---|
| 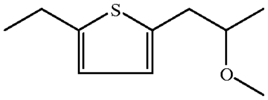 | 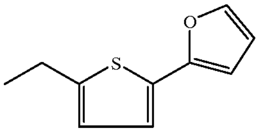 |
| 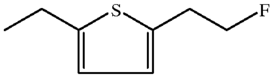 | 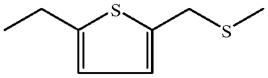 |
| 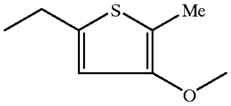 | 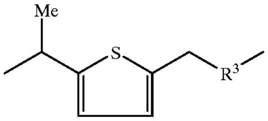 |
TABLE 5
(5)
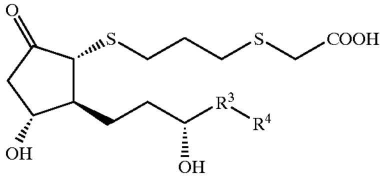
| —R³—R⁴ | | |
|---|---|---|
| 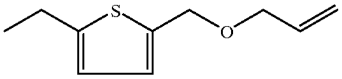 | 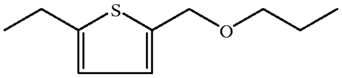 | 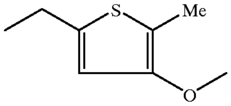 |
| 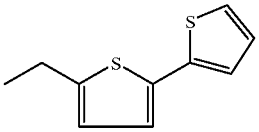 | 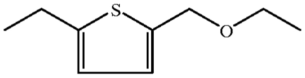 | 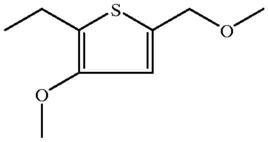 |
| 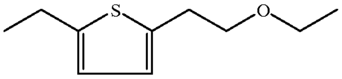 | 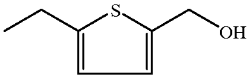 | 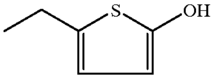 |
| 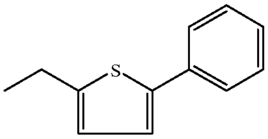 | 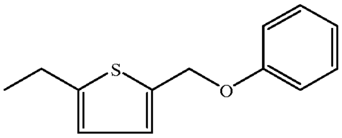 | 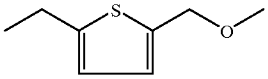 |

TABLE 5-continued
(5)
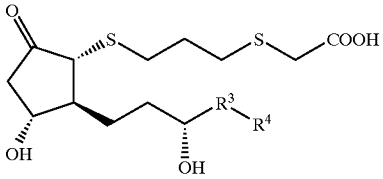
—$R^3$—$R^4$
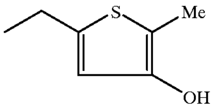
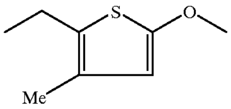
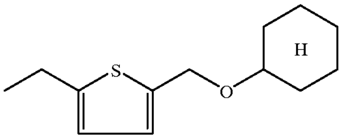
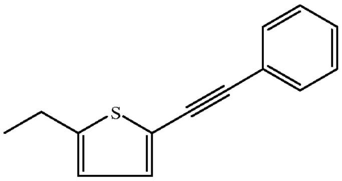
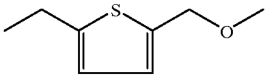
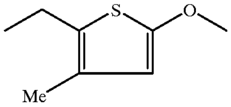
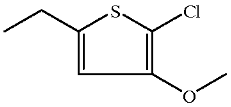
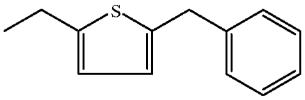
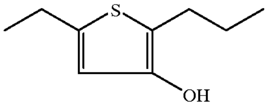
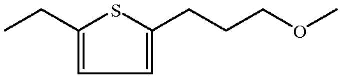
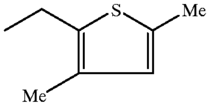
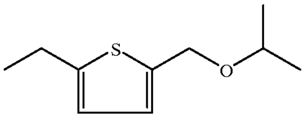
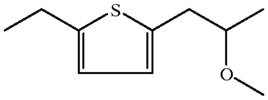
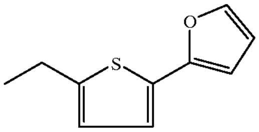
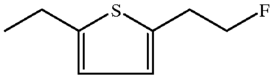
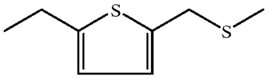
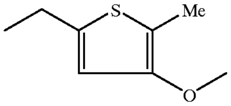
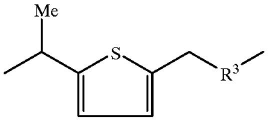

Salts

The compounds of the present invention of the general formula (I) may be converted into the corresponding salts by known methods. Non-toxic and water-soluble salts are preferable. Suitable salts, for example, are as follows: salts of alkali metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

Cyclodextrin Clathrate

Cyclodextrin clathrates of 3,7-dithiaprostanoic acid derivatives of the formula (I) may be prepared by the method described in the specification of Japanese Patent Application Kokoku Sho 50-3362, 52-31404 or 61-52146 using α, β- or γ-cyclodextrin or a mixture thereof. Converting into the corresponding cyclodextrin clathrates serves to increase the stability and solubility in water of the compounds, and therefore it is useful in the use for pharmaceuticals.

Process for the Preparation (1) Among the compounds of the formula (I) of the present invention, the compounds of the formula (Ia)

(Ia)

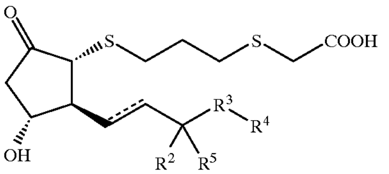

(wherein, all the symbols are the same meaning as defined hereinbefore.) may be prepared by hydrolysis of the compounds of the formula (Ib)

(Ib)

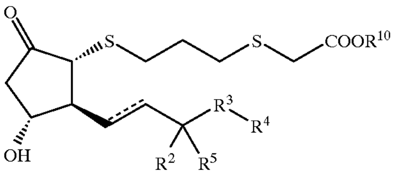

(wherein, $R^{10}$ is C1~6 alkyl and the other symbols are the same meaning as defined hereinbefore.) using an enzyme.

Hydrolysis using an enzyme is well known, it may be carried out, for example, in mixture solution of an organic water-admissible solvent (ethanol, dimethylsulfoxide etc.) and water in the presence or absence of buffer using an enzyme which can decompose ester bond (esterase, lipase etc.) at 0~50° C.

(2) Among the compounds of the formula (I) of the present invention, the compounds of the formula (Ic)

(Ic)

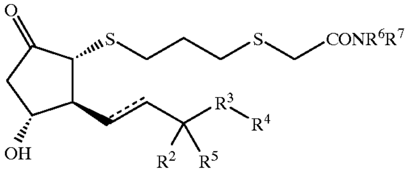

(wherein, all the symbols are the same meaning as defined hereinbefore.) may be prepared by amidation of the compounds of the formula (Ia)

(Ia)

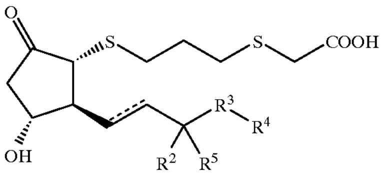

(wherein, all the symbols are the same meaning as defined hereinbefore.) with the compounds of the formula (III)

$HNR^6R^7$ (III)

(wherein, all the symbols are the same meaning as defined hereinbefore.)

Amidation is well known, it may be carried out, for example, in an organic solvent (tetrahydrofuran (THF), methylene chloride, benzene, acetone, acetonitrile or mixture thereof etc.) in the presence or absence of tertiary amine (dimethylaminopyridine, pyridine, triethylamine etc.) using a condensation agent (1-ethyl-3-[3-(dimethylamino)propyl] carbodiimido (EDC), 1,3-dicyclohexylcarbodiimido (DCC) etc.) at 0~50°C.

(3) Among the compounds of the formula (I) of the present invention, the compounds of the formula (Ib)

(Ib)

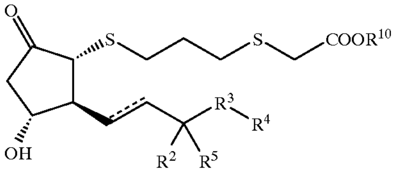

(wherein, all the symbols are the same meaning as defined hereinbefore.) may be prepared by hydrolysis of the compounds of the formula (II)

(II)

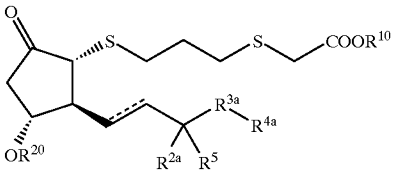

(wherein, $R^{10}$ is the same meaning as defined hereinbefore, $R^{2a}$ is hydrogen, or hydroxy group protected by a protecting group which is removable in an acidic condition;

$R^{20}$ is a protecting group which is removable in an acidic condition;

$R^{3a}$ is single bond or C1~6 alkylene;

$R^{4a}$ is (i) C1–8 alkyl, C2–8 alkenyl or C2–8 alkynyl substituted by one to three substituent(s) selected from the group consisting of C1~6 alkyloxy and halogen atom, (ii) phenyloxy or C3~7 cycloalkyloxy, (iii) furyl, furyloxy, thienyl, thienyloxy, naphthyl, naphthyloxy, phthalanyl or phthalanyloxy, (iv) phenyl, phenyloxy, C3~7 cycloalkyl or C3~7 cycloalkyloxy substituted by one to three substituent(s) selected from the group consisting of the following groups:

C1~6 alkyl,
C2~6 alkenyl,
C2~6 alkynyl,
C1~6 alkyloxy,
C1~6 alkyloxy-C1~6 alkyl,
C1~6 alkyloxy-C1~6 alkyloxy,
C2~6 alkenyloxy-C1~6 alkyl,
C1~6 alkyl substituted by 1–3 of hydroxy group protected by a protecting group which is removable in an acidic condition,
C1~6 alkyl substituted by 1–3 of halogen atom (s),
C1~6 alkylthio,
C1~6 alkylthio-C1~6 alkyl,
C1~6 alkylthio-C1~6 alkyloxy,
C2~6 alkenylthio-C1~6 alkyl,
C1~6 alkylsulfonyl,
halogen,
trihalomethyl,
cyano,
nitro,
amino protected by a protecting group which is removable in an acidic condition,
hydroxy group protected by a protecting group which is removable in an acidic condition,
C3~7 cycloalkyl,
C3~7 cycloalkyloxy,
C3~7 cycloalkyl-C1~6 alkyl,
C3~7 cycloalkyloxy-C1~6 alkyl,
phenyl,
phenyloxy,
phenyl-C1~6 alkyl,
phenyl-C2~6 alkenyl,
phenyl-C2~6 alkynyl,
phenyloxy-C1~6 alkyl,
phenyloxy-C2~6 alkenyl,
phenyloxy-C2~6 alkynyl,
furyl,
furyloxy,
furyl-C1~6 alkyl,
furyloxy-C1~6 alkyl,
thienyl,
thienyloxy,
thienyl-C1~6 alkyl and
thienyloxy-C1~6 alkyl (the above phenyl, furyl, thienyl or cycloalkyl may be substituted by one to three substituent (s) selected from the group consisting of C1~6 alkyl, C1~6 alkyloxy, C1~6 alkyloxy-C1~6 alkyl, nitro, halogen, trihalomethyl, amino protected by a protecting group which is removable in an acidic condition and hydroxy group protected by a protecting group which is removable in an acidic condition.); or (v) furyl, furyloxy, thienyl, thienyloxy, naphthyl, naphthyloxy, phthalanyl or phthalanyloxy substituted by one to three substituent(s) selected from the group consisting of the following group:

C1~6 alkyl,
C2~6 alkenyl,
C2~6 alkynyl,
C1~6 alkyloxy,
C1~6 alkyloxy-C1~6 alkyl,
C1~6 alkyloxy-C1~6 alkyloxy,
C2~6 alkenyloxy-C1~6 alkyl,
C1~6 alkyl substituted by 1–3 of hydroxy group protected by a protecting group which is removable in an acidic condition,
C1~6 alkyl substituted by 1–3 of halogen atom (s),
C1~6 alkylthio,
C1~6 alkylthio-C1~6 alkyl,
C1~6 alkylthio-C1~6 alkyloxy,
C2~6 alkenylthio-C1~6 alkyl,
C1~6 alkylsulfonyl,
halogen,
trihalomethyl,
cyano,
nitro,
amino protected by a protecting group which is removable in an acidic condition,
hydroxy group protected by a protecting group which is removable in an acidic condition,
C3~7 cycloalkyl,
C3~7 cycloalkyloxy,
C3~7 cycloalkyl-C1~6 alkyl,
C3~7 cycloalkyloxy-C1~6 alkyl,
phenyl,
phenyloxy,
phenyl-C1~6 alkyl,
phenyl-C2~6 alkenyl,
phenyl-C2~6 alkynyl,
phenyloxy-C1~6 alkyl,
phenyloxy-C2~6 alkenyl,
phenyloxy-C2~6 alkynyl,
furyl,
furyloxy,
furyl-C1~6 alkyl,
furyloxy-C1~6 alkyl,
thienyl,
thienyloxy,
thienyl-C1~6 alkyl and
thienyloxy-C1~6 alkyl (the above phenyl, furyl, thienyl or cycloalkyl may be substituted by one to three substituent (s) selected from the group consisting of C1~6 alkyl, C1~6 alkyloxy, C1~6 alkyloxy-C1~6 alkyl, nitro, halogen, trihalomethyl, amino protected by a protecting group which is removable in an acidic condition and hydroxy group protected by a protecting group which is removable in an acidic condition.)

and the other symbols are the same meaning as defined hereinbefore; with the proviso that when $R^{2a}$ is hydrogen, C1~6 alkylene represented by $R^{3a}$ may be substituted by a hydroxy group protected by a protecting group which is removable in an acidic condition.)

in an acid condition.

The protecting groups of hydroxy and amino which are removable in an acidic condition are, for example, t-butyldimethylsilyl, triphenylmethyl and t-butyloxycarbonyl etc.

Hydrolysis in an acidic condition is well known. It may be carried out, for example, in a water-miscible organic solvent (THF, methanol, ethanol, dimethoxyethane, acetonitrile or mixture thereof etc.) using an inorganic acid (e.g. hydrochloric acid, phosphoric acid, hydrofluoric acid, hydrochloride-pyridine complex etc.) or an organic acid (acetic acid, tosylic acid, trifluoroacetic acid etc.) at 0–50° C.

The compounds of the formula (II) may be prepared according to the following reaction scheme (A).

In the reaction scheme, "Bu" is n-butyl, "t-Bu" is t-butyl and the other symbols are the same meaning as defined hereinbefore.

That is to say, the compounds of the formula (Id)

(Id)

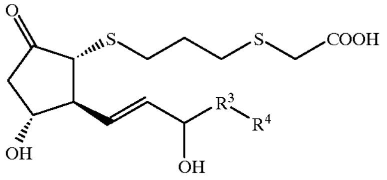

(wherein, all the symbols are the same meaning as defined hereinbefore.) may be prepared by hydrolysis of the compounds of the formula (XVI)

Reaction Scheme A

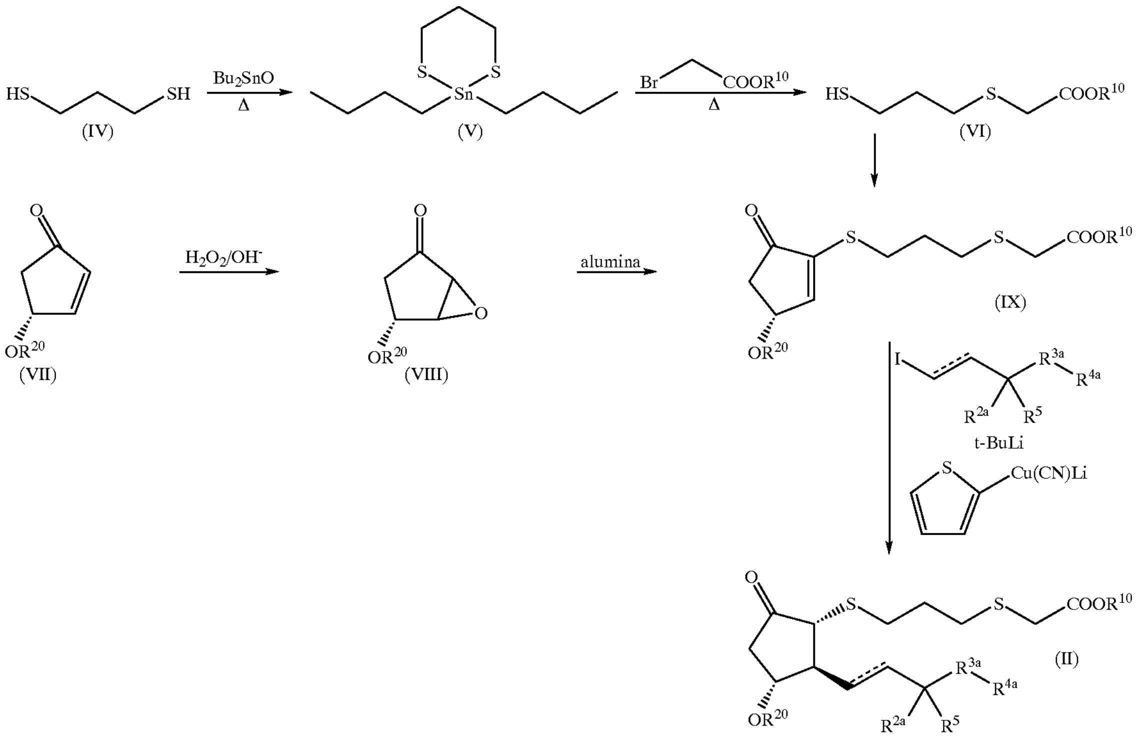

(IV) (V) (VI) (VII) (VIII) (IX) (II)

(4) Among the compounds of the formula (I) of the present invention, the compounds wherein the bond between 13–14-position is double bond, $R^2$ is hydroxy and $R^5$ is hydrogen, i.e. the compounds of the formula (Id) may be prepared by the following method beside to the above mentioned method.

(XVI)

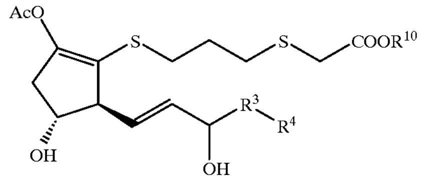

(wherein, Ac is acetyl and the other symbols are the same meaning as defined hereinbefore.) with an enzyme.

Hydrolysis using an enzyme is well known. It may be carried out, for example, in a water-miscible organic solvent (DMSO, ethanol etc.) in the presence or absence of buffer (phosphate buffer etc.) using an enzyme (lipase, esterase etc.) at 0–50° C.

The compounds of the formula (XVI) may be prepared according to the following reaction scheme (B).

Reaction Scheme B

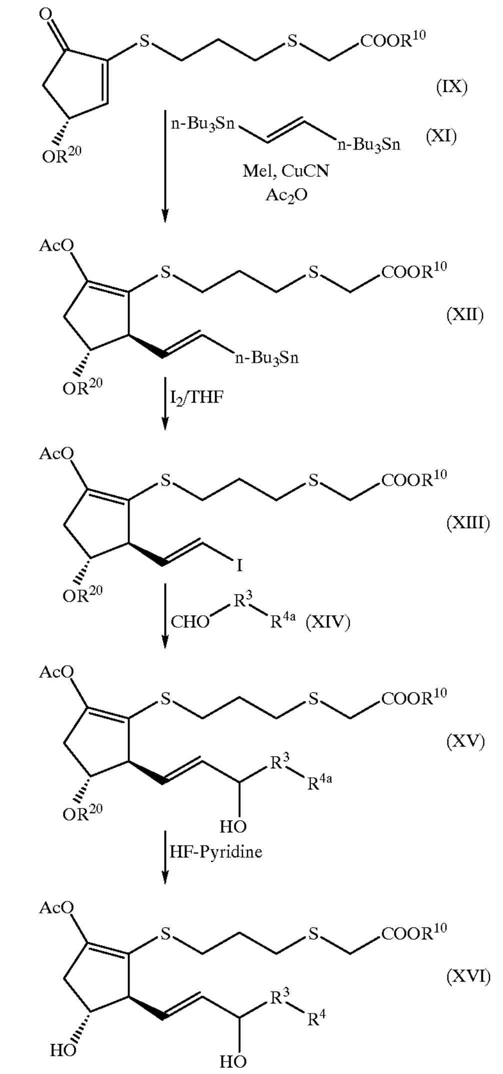

(IX)

(XI)

(XII)

(XIII)

(XIV)

(XV)

(XVI)

In the reaction scheme, "Ac" is acetyl and the other symbols are the same meaning as defined hereinbefore.

In each reaction in the present specification, reaction products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Starting Materials and Reagents

The starting materials and reagents in the present invention are known per se or may be prepared by known methods.

Pharmacological Activities

The compounds of the present invention of the formula (I) can bind strongly and show an activity on the EP4 subtype receptor which is one of the $PGE_2$ receptors.

For example, in a standard laboratory test, such effects of the compound of the present invention were confirmed by binding assay using cell expressing the prostanoid receptor subtypes. (i) Binding assay using cell expressing the prostanoid receptor subtypes The preparation of membrane fraction was carried out according to the method of Sugimoto et al [J. Biol. Chem. 267, 6463–6466 (1 992)], using CHO cell expressing prostanoid receptor subtype (mouse $EP_3\alpha$, EP4).

The standard assay mixture containing membrane fraction (0.5 mg/ml), [$^3$H]-$PGE_2$ in a final volume of 200 $\mu$l was incubated for 1 hour at room temperature. The reaction was terminated by addition of 3 ml of ice-cold buffer. The mixture was rapidly filtered through a glass filter (GF/B). The radioactivity associated with the filter was measured by liquid scintillation counter.

Kd and Bmax values were determined from Scatchard plots [Ann. N.Y. Acad. Sci., 51, 660 (1949)]. Non-specific binding was calculated as the amount bond in the presence of an excess (2.5 $\mu$M) of unlabeled $PGE_2$. In the experiment for competition of specific [$^3$H]-$PGE_2$ binding by the compounds of the present invention, [$^3$H]-$PGE_2$ was added at a concentration of 2.5 nM and the compound of the present invention was added at a various concentration.

The following buffer was used in all reactions. Buffer: 10 mM potassium phosphate (pH 6.0), 1 mM EDTA, 10 mM $MgCl_2$, 0.1 M NaCl The dissociation constant (Ki) of each compound was calculated by the following equation.

$$Ki=IC_{50}/(1+([C]/Kd)$$

The results are shown in Table 8.

TABLE 8 dissociation constant to receptor

| Example No. (more polar) | dissociation constant Ki ($\mu$M) EP3$\alpha$ | dissociation constant Ki ($\mu$M) EP4 |
|---|---|---|
| 2 | 1.2 | 0.0097 |
| 2(f) | 0.51 | 0.0099 |
| 2(l) | 2.2 | 0.011 |
| 2(r) | 0.97 | 0.001 |
| 2(ii) | 0.25 | 0.0028 |
| 2(rr) | 1.9 | 0.0042 |
| 2(tt) | 0.9 | 0.0065 |
| 2(bbb) | 0.23 | 0.0003 |
| 2(lll) | 6.2 | 0.0014 |
| 2(mmm) | >10 | 0.04 |

Toxicity

The toxicity of the compounds of the formula (I) of the present invention is very low and therefore, it is confirmed that these compounds are safe for use as medicine.

Application for Pharmaceuticals

The compounds of the present invention of the formula (I) can bind and show the activity on the $PGE_2$ receptor. Particularly, they bind EP4 subtype receptor strongly, so they are useful for the prevention and/or treatment of immunological diseases (autoimmune diseases such as ALS, multiple sclerosis, Sjoegren's syndrome, chronic rheumarthrosis and systemic lupus erythematosus etc. and rejection after organ transplantation etc.), asthma, abnormal bone formation, neuronal cell death, liver damage, nephritis, hypertension, myocardiac ischemia and sleeping disorder etc.

Among the compounds of the present invention of the formula (I), compounds which bind weakly to receptor subtypes except for EP4 receptor do not express other effects and therefore such compounds are expected to be an agent having less side effect.

For the purpose above described, the compounds of the formula (I) of the present invention, non-toxic salts thereof, or CD clathrate thereof may be normally administered systematically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 μg and 100 mg, by oral administration, up to several times per day, and between 0.1 μg and 10 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as solid compositions, liquid compositions or other compositions for oral administration, or as injections, liniments or suppositories etc. for parenteral administration.

Solid compositions for oral administration include compressed tablets, pills, capsules, dispersible powders, and granules.

Capsules contain hard capsules and soft capsules.

In such compositions, one or more of the active compound(s) is or are, admixed with at least one inert diluent such as lactose, mannitol, mannit, glucose, hydroxypropyl cellulose, microcrystalline cellulose, starch, polyvinylpyrrolidone, magnesium metasilicate aluminate.

The compositions may also comprise, as is normal practice, additional substances other than inert diluents: e.g. lubricating agents such as magnesium stearate, disintegrating agents such as cellulose calcium glycolate, and assisting agents for dissolving such as glutamic acid, asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent (s) commonly used in the art (for example, purified water, ethanol etc.). Besides inert diluents, such compositions may also comprise adjuvants such as wetting agents, suspending agents, sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSORBATE80 (registered trade mark) etc.

Such compositions may comprise additional diluents: e.g. preserving agents, wetting agents, emulsifying agents, dispersing agents, stabilizing agent, assisting agents such as assisting agents for dissolving (for example, glutamic acid, asparaginic acid). They may be sterilized for example, by filtration through a bacteria-retaining filter, by incorporation of sterilizing agents in the compositions or by irradiation. They may also be manufactured in the form of sterile solid compositions which can be dissolved in sterile water or some other sterile diluent for injection immediately before use.

Other compositions for parenteral administration include liquids for external use, and endermic liniments, ointments, suppositories and pessaries which comprise one or more of the active compound(s) and may be prepared by known methods.

REFERENCE EXAMPLES AND EXAMPLES

The following reference examples and examples are intended to illustrate, but not limit, the present invention.

The solvents in parentheses show the developing or eluting solvents and the ratios of the solvents used are by volume in chromatographic separations. Unless otherwise specified, "NMR" was measured in a solution of $CDCl_3$. In the formula, "Tr" is triphenylmethyl, "THP" is tetrahydropyranyl", "TBS" is t-butyldimethylsilyl, "Et" is ethyl and the other symbols are as defined hereinbefore.

Reference Example 1

1-bromo-3-methoxymethylbenzene

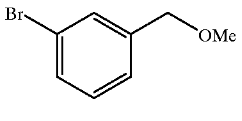

To a solution of 3-bromobenzylbromide (15.0 g, 60 mmol) in methanol-dimethoxyethane (DME) (30 ml+10 ml), sodium methylate (4.9 g, 90 mmol) was added under cooling with ice. The solution was stirred at room temperature for 1 hour. The reaction mixture was poured into water. The reaction mixture was extracted with ether. The organic layer was washed with an aqueous saturated solution of sodium chloride, dried over magnesium sulfate. The solvent was distilled off to give the title compound (12.1 g, 100%) having the following physical data.

TLC: Rf 0.74 (ethyl acetate:hexane=1:4); NMR: δ 7.50 (s, 1H), 7.42 (dt, J=8, 2 Hz, 1H), 7.3–7.2 (m, 2H), 4.43 (s, 2H), 3.40 (s, 3H).

Reference Example 2

(2S)-3-(3-methoxymethylphenyl)-1-triphenylmethoxypropan-2-ol

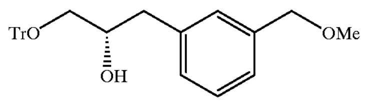

Magnesium (1.41 g, 58 mmol) was heated and dried under vacuum. Thereto, anhydrous THF (30 ml) and dibromoethane (a few drops) were added. A solution of the compound prepared in Reference Example 1 (9.65 g, 48 mmol) in anhydrous THF (30 ml) was added dropwise thereto for 45 minutes. The obtained solution was added to a suspension of copper iodide (0.76 g, 4 mmol) in anhydrous THF (30 ml) under cooling with ice. The mixture was stirred for 30 minutes. Thereto, a solution of S-(-)-glycidyl tolytyl ether (12.7 g, 40 mmol) in anhydrous THF (30 ml) was added. The mixture was stirred for 1 hour and poured into an aqueous saturated solution of ammonium chloride. The reaction mixture was extracted with ethyl acetate. The organic layer was washed with an aqueous saturated solution of sodium chloride, dried over magnesium sulfate. The solvent was distilled off to give the title compound (19.5 g) having the following physical data.

TLC: Rf 0.29 (ethyl acetate:hexane=1:4); NMR: δ 7.5–7.1 (m, 19H), 4.40 (s, 2H), 4.1–3.9 (m, 1H), 3.37 (s, 3H), 3.3–3.1 (m, 2H), 2.9–2.7 (m, 2H), 2.23 (brd, 1H).

Reference Example 3

(2S)-3-(3-methoxymethylphenyl)propan-1,2-diol

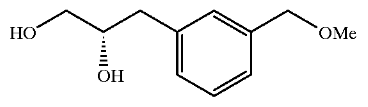

To a solution of the compound prepared in Reference Example 2 (19.5 g) in anhydrous THF (10 ml), acetic acid (80 ml) and water (10 ml) were added. The mixture was heated at 60° C. for 6 hours. To the reaction mixture, water (40 ml) was added. The mixture was cooled to room temperature. The precipitate was filtered and the filtrate was concentrated. After filtering the precipitate again, the obtained oil was concentrated with toluene to remove the solvent entirely and to give the title compound (8.9 g) having the following physical data.

TLC: Rf 0.64 (ethyl acetate:hexane=2:1).

Reference Example 4

(2S)-3-(3-methoxymethylphenyl)-1-acetyloxypropan-2-ol

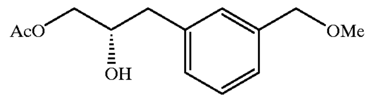

A solution of the compound prepared in Reference Example 3 (8.9 g) and 2,4,6-collidine (10.6 ml, 80 mmol) in methylene chloride (120 ml) was cooled to −70° C. Thereto, acetyl chloride (4.0 ml, 56 mmol) was added dropwise. The mixture was stirred for 15 minutes. Thereto, methanol was added. The solution was warmed to ° C. The reaction mixture was washed with 1 N aqueous HCl and an aqueous saturated solution of sodium chloride, respectively, dried over magnesium sulfate. The solvent was distilled off to give the title compound (10.8 g) having the following physical data.

TLC: Rf 0.64 (ethyl acetate:hexane=2:1); NMR: δ 7.4–7.1 (m, 4H), 4.43 (s, 2H), 4.25–3.95 (m, 3H), 3.41 (s, 3H), 2.9–2.8 (m, 2H), 2.12 (s, 3H).

Reference Example 5

(2S)-3-(3-methoxymethylphenyl)-1-acetyloxy-2-(2-tetrahydropyranyloxy)-propane

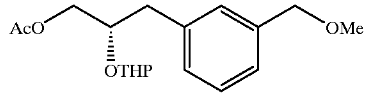

To a solution of the compound prepared in Reference Example 4 (10.8 g) in methylene chloride (40 ml), dihydropyran (5.5 ml, 60 mmol) and pyridinium p-toluenesulfonate (0.50 g) were added. The mixture was stirred for 4 hours. The solution was concentrated, diluted with ethyl acetate, washed with water and an aqueous saturated solution of sodium hydrogen carbonate, respectively, and dried over sodium sulfate. The solvent was distilled off. The residue was purified by silica gel column chromatography to give the title compound (14.0 g) having the following physical data.

TLC: Rf 0.53 (ethyl acetate:hexane:methylene chloride=1:2:2); NMR: δ 7.3–7.1 (m, 4H), 4.85–4.8 and 4.45–4.0 (m, 1H), 4.43 (s, 2H), 4.25–3.85 and 3.5–3.2 (m, 5H), 3.39 (s, 3H), 3.05–2.8 (m, 2H), 2.10 and 2.08 (s, 3H), 1.9–1.4 (m, 6H).

Reference Example 6

(2S)-3-(3-methoxymethylphenyl)-2-(2-tetrahydropyranyloxy)propane-1-ol

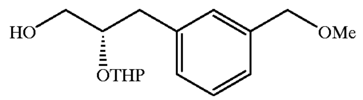

To a solution of the compound prepared in Reference Example 5 (14.0 g) in methanol (40 ml), 2N solution of sodium hydroxide (5 ml) was added. The mixture was stirred at room temperature for 1 hour. The solvent was distilled off under reduced pressure. The reaction mixture was diluted with ether, washed with water and an aqueous saturated solution of sodium chloride, respectively, and dried over sodium sulfate. The solution was concentrated. The rest oil was purified by silica gel column chromatography to give the title compound (11.0 g, <98%) having the following physical data.

TLC: Rf 0.51, 0.41 (diastereomeric mixture came from THP, ethyl acetate:hexane=2:1); NMR: δ 7.3–7.1 (m, 4H), 4.85–4.8 and 4.25–4.2 (m, 1H), 4.42 (s, 2H), 4.05–3.4 (m, 5H), 3.38 (s, 3H), 3.06 (dd, J=14, 6 Hz, 1H), 2.85 (dd, J=14, 8 Hz, 1H), 2.8–2.7 and 2.15–2.05 (m, 1H), 1.9–1.4 (m, 6H).

Reference Example 7

(2S)-3-(3-methoxymethylphenyl)-2-(2-tetrahydropyranyloxy)propan-1-al

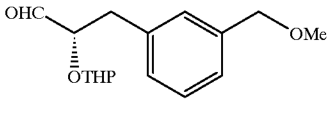

A solution of oxalyl chloride (6.8 ml, 78 mmol) in methylene chloride (150 ml) was cooled to −78° C., A solution of anhydrous DMSO (11.1 ml, 156 mmol) in methylene chloride (30 ml) was added dropwise thereto for 15 minutes. The mixture was stirred for 15 minutes. A solution of the compound prepared in Reference Example 6 (11.0 g, 39 mmol) in methylene chloride (40 ml) was added dropwise thereto for 35 minutes. In addition, the solution was stirred for 10 minutes. Thereto, triethylamine (32 ml) was added. The reaction mixture was warmed to −40° C., stirred for 45 minutes and poured into 1N aqueous HCl and extracted with mixture solvent of ether-hexane. The organic layer was washed with water, an aqueous saturated solution of sodium hydrogen carbonate and an aqueous saturated solution of sodium chloride, respectively, and dried over sodium sulfate. The solvent was distilled off to give the title compound (11.1 g) having the following physical data.

TLC: Rf 0.45 (ethyl acetate:hexane=1:2); NMR: δ 9.75–9.0 (m, 1H), 7.3–7.1 (m, 4H), 4.8–4.75 and 4.35–4.3 (m, 1H), 4.43 (s, 2H), 4.45–4.3 and 4.1–4.0 (m, 1H), 3.95–3.9 and 3.5–3.4 (m, 1H), 3.40 (s, 3H), 3.3–2.8 (m, 3H), 1.9–1.3 (m, 6H).

Reference Example 8

(3S)-1,1-dibromo-4-(3-methoxymethylphenyl)-3-(2-tetrahydropyranyloxy)-1-butene

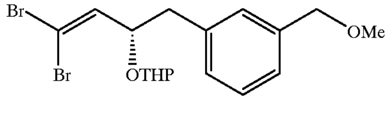

A solution of tetrabromomethane (39.8 g, 0.12 mol) in methylene chloride (150 ml) was cooled to −20° C. A solution of triphenylphosphine (63 g, 0.24 mol) in methylene chloride (100 ml) was added dropwise thereto for 20 minutes. The obtained red-blown solution was cooled to −40° C. A solution of the compound prepared in Reference Example 7 (11.1 g) and triethylamine (5.6 ml, 40 mmol) in methylene chloride (40 ml) was added dropwise thereto. The mixture was stirred for 10 minutes. Thereto, triethylamine (11.7 ml) and methanol (9.8 ml) were added. The obtained blown solution was poured into the mixture solvent of ether-hexane with stirring vigorously. The solid was removed with filter. The filtrate was concentrated. The residue was purified by silica gel column chromatography to give the title compound (13.6 g, 78%) having the following physical data.

TLC: Rf 0.36 (ethyl acetate:hexane=1:9).

Reference Example 9

(3S)-4-(3-methoxymethylphenyl)-3-(2-tetrahydropyranyloxy)-1-butyne

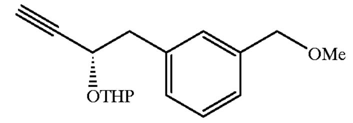

A solution of the compound prepared in Reference Example 8 (13.5 g, 31.1 mmol) in anhydrous THF (90 ml) was cooled to −78° C. A solution of n-butyllithium in hexane (1.61 M, 42.5 ml, 68.4 mmol) was added dropwise thereto for 20 minutes. The mixture was stirred for 10 minutes. The reaction mixture was poured into an aqueous saturated solution of ammonium chloride and extracted with ethyl acetate. The organic layer was washed with an aqueous saturated solution of sodium chloride, and dried over sodium sulfate. The solvent was distilled off. The residue was purified by silica gel column chromatography to give the title compound (8.9 g) having the following physical data.

TLC: Rf 0.50, 0.44 (ethyl acetate:hexane=1:4).

Reference Example 10

(3S)-4-(3-methoxymethylphenyl)-1-butyn-3-ol

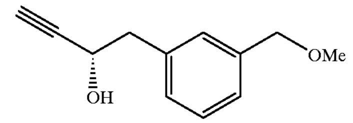

The compound prepared in Reference Example 9 (8.9 g) was dissolved in dioxane (10 ml) and methanol (10 ml). Thereto, 4N HCl-dioxane (2 ml) was added at room temperature. The mixture was stirred for 1 hour. The reaction mixture was diluted with water and extracted with ethyl acetate. The organic layer was washed with an aqueous saturated solution of sodium hydrogen carbonate and an aqueous saturated solution of sodium chloride, respectively, and dried over sodium sulfate. The solvent was distilled off. The residue was purified by silica gel column chromatography to give the title compound (5.6 g) having the following physical data.

TLC: Rf 0.40 (ethyl acetate:hexane=1:2).

Reference Example 11

(3S)-4-(3-methoxymethylphenyl)-3-t-butyldimethylsilyloxy-1-butyne

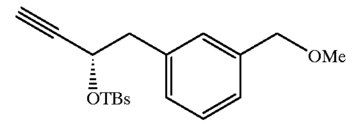

To a solution of the compound prepared in Reference Example 10 (5.64 g, 29 mmol) and imidazole (3.0 g, 44 mmol) in DMF (30 ml), t-butyldimethyl-silylchloride (5.3 g, 35 mmol) was added. The mixture was stirred at room temperature. The reaction mixture was poured into water and extracted with ethyl acetate. The organic layer was washed by water and an aqueous saturated solution of sodium chloride, respectively, and dried over sodium sulfate. The solvent was distilled off. The residue was purified by silica gel column chromatography to give the title compound (7.82 g, 83%) having the following physical data.

TLC: Rf 0.73 (ethyl acetate:hexane=1:4); NMR: δ 7.3–7.1 (m, 4H), 4.5–4.45 (m, 1H), 4.44 (s, 2H), 3.37 (s, 3H), 3.0–295 (m, 2H), 2.41 (d, J=2 Hz, 1H), 0.83 (s, 9H), −0.02 (s, 3H), −0.08 (s, 3H).

Reference Example 12

(3S)-1-iodo-4-(3-methoxymethylphenyl)-3-t-butyldimethylsilyloxy-1E-butene

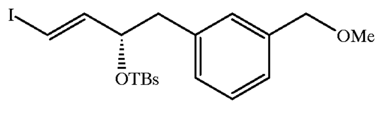

A solution of the compound prepared in Reference Example 11 (7.7 g, 25 mmol) in THF (30 ml) was added to a suspension of zirconocene chloride hydride (7.81 g, 30 mmol) in anhydrous THF (15 ml) at room temperature. The mixture was stirred for 45 minutes and cooled to 0° C. A solution of iodine (6.43 g, 25 mmol) in THF was added dropwise thereto. The mixture was stirred at room temperature for 15 minutes. Thereto, hexane was added. The precipitate was filtrated with silica gel. The filtrate was concentrated. The residue was purified by silica gel column chromatography to give the title compound (9.77 g, 89%) having the following physical data.

TLC: Rf 0.61 (ethyl acetate:hexane=1:9); NMR: δ 7.3–7.05 (m, 4H), 6.56 (dd, J=15, 5 Hz, 1H), 6.19 (dd, J=15, 1 Hz, 1H), 4.43 (s, 2H), 4.3–4.15 (m, 1H), 3.38 (s, 3H), 2.8–2.7 (m, 2H), 0.83 (s,9H), −0.08 (s, 3H), −0.11 (s, 3H).

Reference Example 13

2,2-dibutyl-2-stanna-1,3-dithian

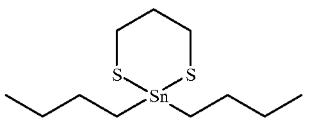

In benzene, 1,3-propandithiol (3.0 g) and dibutylstannum oxide (6.9 g) were refluxed. The reaction mixture was concentrated under reduced pressure to give the title compound (9.38 g) having the following physical data.

TLC: Rf 0.68 (hexane:ethyl acetate=9:1).

Reference Example 14 methyl 6-mercapt-3-thiahexanoate

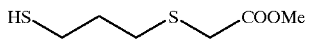

To a solution of 2,2-dibutyl-2-stanna-1,3-dithian (prepared in Reference Example 13.) (9.38 g) in anhydrous dimethylformamide (DMF) (20 ml), bromoacetic acid methyl (6.36 g) was added. The mixture was stirred at 100° C. for 3 hours. The reaction mixture was left for cooling, Water was added thereto. The mixture was stirred for 1 hour and extracted with ethyl acetate. The organic layer was washed, dried over and concentrated under reduced pressure. The residue was purified by silica gel column chromatography (hexane-ethyl acetate) to give the title compound (2.61 g) having the following physical data.

TLC: Rf 0.60 (hexane: ethyl acetate=4:1).

Reference Example 15 methyl 7-(4R-t-butyldimethylsilyloxy-2-cyclopentenon-2-yl)-3,7-dithiaheptanoate

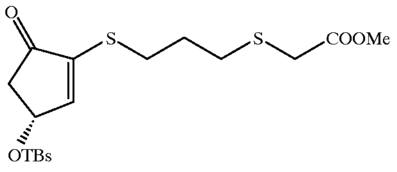

A solution of 4R-t-butyldimethylsilyloxy-2-cyclopentenone (2.76 g) in methanol (40 ml) was cooled with ice. Thereto, hydroperoxide (31%, 5 ml) and 1N solution of sodium hydroxide (0.05 ml) were added. The mixture was stirred at the same temperature for 1.5 hours. An aqueous saturated solution of ammonium chloride was added to the reaction mixture. The mixture was extracted with ethyl acetate. The organic layer was washed, dried over and concentrated under reduced pressure. The residue was dissolved in chloroform (35 ml). To the solution, a solution of methyl 6-mercapt-3-thiahexanoate (prepared in Reference Example 14) (2.34 g) in chloroform (10 ml) and activated alumina (13 g) were added. The mixture was stirred at room temperature overnight. The reaction mixture was filtered. The filtrate was concentrated under reduced pressure and purified by silica gel column chromatography (hexane-ethyl acetate) to give the title compound (3.21 g) having the following physical data.

TLC: Rf 0.39 (hexane:ethyl acetate=4:1).

Reference Example 16

11 α, 15 α-bis(t-butyldimethylsilyloxy)-9-oxo-16-(3-methoxymethylphenyl)-17,18,19,20-tetranor-3,7-dithiaprost-13E-enoic acid methyl ester

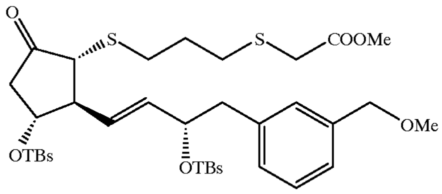

Under an atmosphere of argon, a solution of t-butyllithium in n-pentane (1.64M, 339 ml, 0.556 mmol) was added dropwise to a solution of the compound prepared in Reference Example 12 (120 mg, 0.278 mmol) in anhydrous ether (1.11 ml, 0.25M) at −78° C. The mixture was stirred for 1 hour. To the reaction solution, anhydrous THF (1.11 ml) was added. A solution of lithium 2-thienylcyanocuprate in THF (0.25M, 1.19 ml, 0.297 mmol) was added dropwise thereto. The obtained solution was stirred for 30 minutes.

To this solution, a solution of methyl 7-(4R-t-butyldimethylsilyloxy-2-cyclopentenon-2-yl)-3,7-dithiaheptanoate (72 mg, 0.185 mmol, prepared in Reference Example 15.) in anhydrous THF (0.74 ml, 0.25M) was added dropwise slowly. The mixture was stirred for 1 hour. An aqueous saturated solution of ammonium chloride was added thereto and warmed to 0° C. after the termination of reaction. The reaction mixture was extracted with hexane. The organic layer was washed by a mixture solution of an aqueous saturated solution of ammonium chloride −28% aqueous solution of ammonium (5:1), an aqueous saturated solution of sodium chloride and dried over sodium sulfate.

The solvent was distilled off under reduced pressure. The residue was purified by silica gel column chromatography (hexane-ethyl acetate) to give the title compound (77 mg, 60%) having the following physical data.

Figure: Pale yellow oil; TLC: Rf 0.47 (hexane:ethyl acetate=4:1); NMR: δ 7.30–7.12 (4H, m), 5.80–5.46 (2H, m), 4.43 (2H, s), 4.28 (1H, m), 4.05 (1H, m), 3.73 (3H, s), 3.38 (3H, s), 3.22 (2H, s), 3.42–2.28 (10H, m), 1.87 (2H, m), 0.89 (9H, s), 0.83 (9H, s), 0.07 and 0.06 (6H, each s), −0.10 (3H, s), −0.26 (3H, s).

Example 1

11 α, 15 α-dihydroxy-9-oxo-16-(3-methoxymethylphenyl)-17,18,19,20-tetranor-3,7-dithiaprost-13E-enoic acid methyl ester

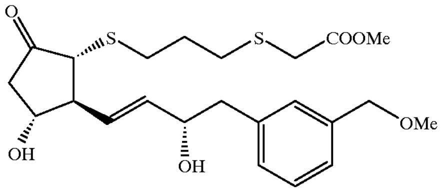

Pyridine (1 ml) and hydrogen fluoride-pyridine complex (2 ml) were added to a solution of the compound prepared in Reference Example 16 (260 mg, 0.373 mmol) in acetonitrile (10 ml) at 0° C. The mixture was stirred at room temperature for 2 hours. The reaction mixture was poured into the cooled mixture solution of ethyl acetate-aqueous saturated solution of ammonium chloride. The mixture was extracted with ethyl acetate. The organic layer was washed by an aqueous saturated solution of sodium hydrogen carbonate and an aqueous saturated solution of sodium chloride, respectively, and dried over anhydrous magnesium sulfate. The solvent was distilled off under reduced pressure. The residue was purified by silica gel column chromatography (hexane-ethyl acetate) to give the title compound (140 mg, 80%; equilibrium mixture with 8-epi compound) having the following physical data.

TLC: Rf 0.49, 0.35 (ethyl acetate:acetic acid=50:1); NMR: δ 7.34–7.11 (4H, m), 5.85–5.46 (2H, m), 4.42 (2H, s), 4.41 (1H, m), 3.97 (1H, m), 3.73 (3H, s), 3.41 (3H, s), 3.22 (2H, s), 3.38–2.15 (10H, m), 1.86 (2H, m).

Example 2

11 α, 15 α-dihydroxy-9-oxo-16-(3-methoxymethylphenyl)-17,18,19,20-tetranor-3,7-dithiaprost-13E-enoic acid

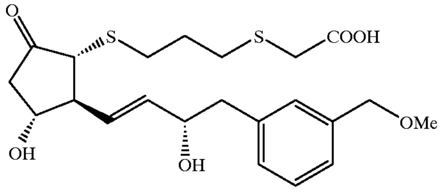

A compound prepared in Example 1 (50 mg, 0.107 mmol) was dissolved into DMSO (2 ml). Thereto, phosphate buffer (2 ml, pH8.0) was added. To this solution, pig liver esterase (70 μl) was added. The mixture was stirred at room temperature for 3 hours. An aqueous saturated solution of ammonium chloride was added thereto. After acidifying the reaction mixture by adding 1N aqueous HCl, the mixture was extracted with ethyl acetate. The organic layer was washed by water and an aqueous saturated solution of sodium chloride, respectively and dried over anhydrous magnesium sulfate. The solvent was distilled off under reduced pressure. The residue was purified by silica gel column chromatography (hexane-ethyl acetate) to give the title compound (33 mg, 67%; equilibrium mixture with 8-epi compound) having the following physical data.

more polar: TLC: Rf 0.18, 0.10 (ethyl acetate:hexane:acetic acid=15:5:1); NMR: δ 7.35–7.11 (4H, m), 5.89–5.47 (2H, m), 4.46 (4H, m), 4.45 (2H, s), 3.95 (1H, m), 3.42 and 3.41 (3H, each s), 3.21 (2H, s), 3.37–2.14 (10H, m), 1.86 (2H, m).

Example 2(a)–2(qqq)

By the similar procedure described in Reference Example 16, Example 1 and Example 2 using the compound prepared in Reference Example 15 and the corresponding iodo compound (prepared by the similar procedure described in Reference Example 1~Reference Example 12.), the compounds having the following physical data were obtained. These compounds are equilibrium mixtures with 8-epi isomers.

Example 2(a)

11 α,15 α-dihydroxy-9-oxo-16-phenyloxy-17,18,19,20-tetranor-3,7-dithiaprost-13E-enoic acid

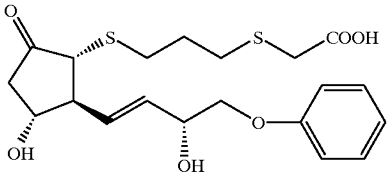

more polar:

TLC: Rf 0.34, 0.27 (ethyl acetate:hexane:acetic acid=15:5:1); NMR: δ 7.29 (t, J=8 Hz, 2H), 6.98 (t, J=8 Hz, 1H), 6.92 (d, J=8 Hz, 2H), 6.0–5. (m,2H), 4.7–4.6 (m,1H), 4.6–4.4 and 4.2–3.9 (m, 3H), 4.7–3.7 (br, 3H),3.22 (br, 3H), 3.45–3.40 and 3.1–2.3 (m, 8H).

Example 2(b)

11 α, 15-dihydroxy-9-oxo-16-(4-methylphenyl)-17,18,19,20-tetranor-3,7-dithiaprost-13E-enoic acid

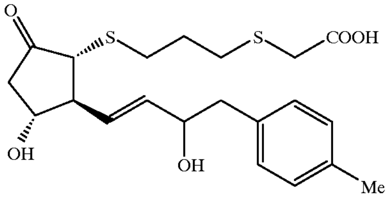

less polar: TLC: Rf 0.70, 0.64 (ethyl acetate:acetic acid=20:1); NMR: δ 7.2–7.0 (m, 4H), 5.80 (dd, J=15, 6 Hz, 1H), 5.53 (dd, J=15, 8 Hz, 1H), 4.5–4.35 and 4.35–4.2 (m, 1H), 4.0–3.8 (m, 1H), 3.9–3.4 (br), 3.22 (s, 2H), 3.4–3.3 and 3.0–2.3 (m, 10H), 2.32 (s, 3H), 2.0–1.8 (m, 2H).

more polar: TLC: Rf 0.68, 0.60 (ethyl acetate:acetic acid=20:1); NMR: δ 7.2–7.0 (m, 4H), 5.84 (dd, J=15, 5 Hz, 1H), 5.63 (dd, J=15, 8 Hz, 1H), 4.5–4.3 (m, 1H), 4.2–4.0 (m, 1H), 3.5–2.8 (br), 3.21 (s, 2H), 3.4–3.3 and 3.0–2.3 (m, 10H), 2.32 (s, 3H), 2.0–1.8 (m, 2H).

Example 2(c)

11 α, 15-dihydroxy-9-oxo-16-(4-chlorophenyl)-17,18,19,20-tetranor-3,7-dithiaprost-13E-enoic acid

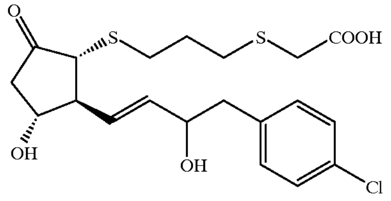

less polar TLC: Rf 0.43, 0.38 (ethyl acetate:hexane:acetic acid=15:5:1); NMR: δ 7.29 (d, J=8 Hz, 2H), 7.16 (d, J=8 Hz, 2H), 5.9–5.7 (m, 1H), 5.59 (dd, J=15, 8 Hz, 1H), 4.5–4.3 (m, 1H), 4.1–3.9 (m, 1H), 4.2–3.4 (br), 3.22 (s, 2H), 3.4–3.3 and 3.0–2.3 (m, 10H), 2.0–1.8 (m, 2H).

more polar: TLC: Rf 0.37, 0.29 (ethyl acetate:hexane:acetic acid=15:5:1); NMR: δ 7.28 (d, J=8 Hz, 2H), 7.16 (d, J=8 Hz, 2H), 5.9–5.7 (m, 1H), 5.62 (dd, J=15, 8 Hz, 1H), 4.5–4.4 (m, 1H), 4.2–4.0 (m, 1H), 3.22 (s, 2H), 3.4–2.8 (br), 3.4–3.3 and 3.0–2.3 (m, 10H), 2.0–1.8 (m, 2H).

Example 2(d)

11 α, 15-dihydroxy-9-oxo-16-(4-methoxyphenyl)-17,18,19, 20-tetranor-3,7-dithiaprost-13E-enoic acid

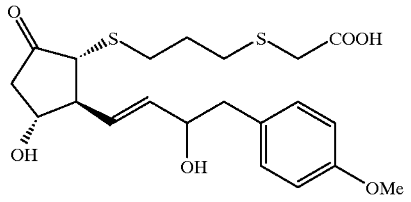

less polar TLC: Rf 0.40, 0.33 (ethyl acetate:hexane:acetic acid=15:5:1); NMR: δ 7.2–7.1 (m, 2H), 6.87 (d, J=8 Hz, 2H), 5.9–5.7 (m, 1H), 5.56 (dd, J×16, 8 Hz, 1H), 4.5–4.4 (m, 1H), 4.4–4.3 and 4.1–3.9 (m, 1H), 3.80 (s, 3H), 3.22 (s, 2H), 3.4–3.3 and 3.0–2.3 (m, 13H), 2.0–1.8 (m, 2H).

more polar: TLC: Rf 0.38, 0.28 (ethyl acetate:hexane:acetic acid=15:5:1); NMR: δ 7.15 (d, J=8 Hz, 2H), 6.86 (d, J=8 Hz, 2H), 5.9–5.75 (m, 1H), 5.62 (dd, J=16, 8 Hz, 1H), 4.5–4.3 and 4.2–4.0 (m, 2H), 3.81 (s, 3H), 3.22 (s, 2H), 3.4–2.7 (br), 3.4–3.3 and 3.0–2.3 (m, 10H), 2.0–1.8 (m, 2H).

Example 2(e)

11 α, 15-dihydroxy-9-oxo-16-(2-methylphenyl)-17,18,19, 20-tetranor-3,7-dithiaprost-13E-enoic acid

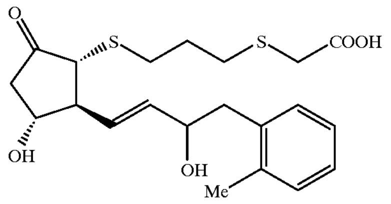

less polar TLC: Rf 0.42, 0.38 (ethyl acetate:acetic acid=50:1); NMR: δ 7.22–7.11 (4H, m), 5.90–5.43 (2H, m), 4.58–4.38 (1H, m), 4.32–3.84 (1H, m), 3.40–2.13 (18H, m), 2.00–1.78 (2H, m).

more polar: TLC: Rf 0.32, 0.26 (ethyl acetate:acetic acid=50:1); NMR: δ 7.21–7.10 (4H, m), 5.95–5.56 (2H, m), 4.56–4.36 (1H, m), 4.20–4.00 (1H, m), 3.40–2.26 (18H, m), 1.98–1.78 (2H, m).

Example 2(f)

11 α, 15-dihydroxy-9-oxo-16-(3-methoxyphenyl)-17,18,19, 20-tetranor-3,7-dithiaprost-13E-enoic acid

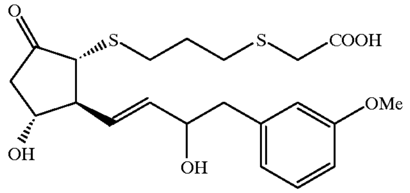

less polar: TLC: Rf 0.34, 0.28 (ethyl acetate:hexane:acetic acid=15:5:1); NMR: δ 7.3–7.2 (m, 1H), 6.85–6.75 (m, 3H), 5.9–5.7 (m, 1H), 5.53 (dd, J=15, 8 Hz, 1H), 4.5–4.4 (m, 1H), 4.35–4.25 and 4.05–3.9 (m, 1H), 3.80 (s, 3H), 3.5–2.8 (br), 3.22 (s, 2H), 3.4–3.3 and 3.0–2.2 (m, 10H), 2.0–1.8 (m, 2H).

more polar: TLC: Rf 0.31, 0.25 (ethyl acetate:hexane:acetic acid=15:5:1); NMR: δ 7.3–7.2 (m, 1H), 6.85–6.75 (m, 3H), 5.9–5.75 (m, 1H), 5.61 (dd, J=15, 8 Hz, 1H), 4.5–4.3 and 4.1–3.9 (m, 2H), 3.79 (s, 3H), 3.7–3.2 (br), 3.22 (s, 2H), 3.4–3.3 and 3.0–2.2 (m, 10H), 2.0–1.8 (m, 2H).

Example 2(g)

11 α, 15-dihydroxy-9-oxo-16-(3-chlorophenyl)-17,18,19, 20-tetranor-3,7-dithiaprost-13E-enoic acid

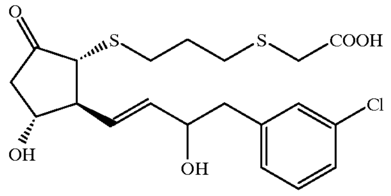

less polar TLC: Rf 0.54, 0.48 (ethyl acetate:acetic acid=100:1); NMR: δ 7.31–7.05 (4H, m), 5.88–5.50 (2H, m), 4.42 and 4.01 (2H, each m), 3.91 (3H, br), 3.22 (2H, s), 3.42–2.15 (10H, m), 1.88 (2H, m).

more polar: TLC: Rf 0.50, 0.40 (ethyl acetate:acetic acid=100:1); NMR: δ 7.30–7.03 (4H, m), 5.88–5.54 (2H, m), 4.44 and 4.07 (2H, each m), 3.49 (3H, br), 3.23 (2H, s), 3.42–2.16 (10H, m), 1.87 (2H, m).

Example 2(h)

11 α, 15-dihydroxy-9-oxo-16-(3-methylphenyl)-17,18,19, 20-tetranor-3,7-dithiaprost-13E-enoic acid

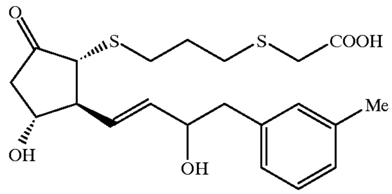

less polar TLC: Rf 0.49, 0.43 (ethyl acetate:acetic acid=100:1); NMR: δ 7.28–6.96 (4H, m), 5.87–5.46 (2H, m), 4.52–3.86 (2H, m), 3.45 (3H, br), 3.21 (2H, s), 3.42–2.14 (10H, m), 2.34 (3H, s), 1.88 (2H, m).

more polar: TLC: Rf 0.48, 0.39 (ethyl acetate:acetic acid=100:1); NMR: δ 7.25–6.96 (4H, m), 5.89–5.53 (2H, m), 4.50–3.96 (2H, m), 3.72 (3H, br), 3.22 (2H, s), 3.40–2.16 (10H, m), 2.33 (3H, s), 1.87 (2H, m).

Example 2(i)

11 α, 15-dihydroxy-9-oxo-16-(2-methoxyphenyl)-17,18,19, 20-tetranor-3,7-dithiaprost-13E-enoic acid

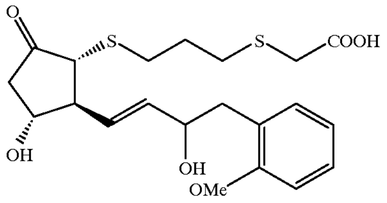

less polar: TLC: Rf 0.46, 0.42 (ethyl acetate:acetic acid=50:1); NMR: δ 7.32–7.08 (2H, m), 6.99–6.84 (2H, m), 5.90–5.42 (2H, m), 4.62–3.88 (2H, m), 3.85 (3H, s), 3.40–2.12 (15H, m), 1.98–1.78 (2H, m).

more polar: TLC: Rf 0.42, 0.38 (ethyl acetate:acetic acid=50:1); NMR: δ 7.32–7.08 (2H, m), 7.00–6.85 (2H, m), 5.87–5.52 (2H, m), 4.68–3.90 (2H, m), 3.87 (3H, s), 3.66–2.12 (15H, m), 1.98–1.78 (2H, m).

Example 2(j)

11 α, 15-dihydroxy-9-oxo-16-(3-thienyl)-17,18,19,20-tetranor-3,7-dithiaprost-13E-enoic acid

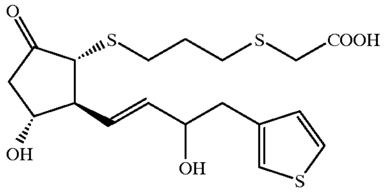

less polar: TLC: Rf 0.31, 0.24 (ethyl acetate:hexane:acetic acid=15:5:1); NMR: δ 7.32 (dd, J=5, 2 Hz, 1H), 7.08 (d, J=2 Hz, 1H), 6.98 (d, J=5 Hz, 1H), 5.9–5.7 (m, 1H), 5.59 (dd, J=15, 8 Hz, 1H), 4.55–4.4 (m, 1H), 4.4–4.25 and 4.1–3.9 (m, 1H), 3.22 (s, 2H), 3.4–3.35 and 3.0–2.2 (m, 13H), 2.0–1.8 (m, 2H).

more polar: TLC: Rf 0.27, 0.18 (ethyl acetate:hexane:acetic acid=15:5:1); NMR: δ 7.30 (dd, J=5, 2 Hz, 1H), 7.08 (d, J=2 Hz, 1H), 6.98 (d, J=5 Hz, 1H), 5.9–5.75 (m, 1H), 5.65 (dd, J=15, 8 Hz, 1H), 4.55–4.4 (m, 1H), 4.45–4.3 and 4.15–4.0 (m, 1H), 3.22 (s, 2H), 3.4–3.35 and 3.2–2.2 (m, 13H), 2.0–1.8 (m, 2H).

Example 2(k)

11 α, 15-dihydroxy-9-oxo-16-(2-thienyl)-17,18,19,20-tetranor-3,7-dithiaprost-13E-enoic acid

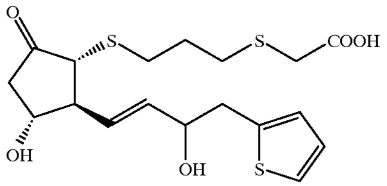

less polar: TLC: Rf 0.47, 0.43 (ethyl acetate:acetic acid=50:1); NMR: δ 7.20 (1H, dd, J=5.2 Hz, 1.2 Hz), 6.97 (1H, dd, J=5.2 Hz, 3.4 Hz), 6.94–6.85 (1H, m), 5.89–5.54 (2H, m), 4.56–3.92 (2H, m), 3.44–2.12 (15H, m), 1.98–1.80 (2H, m).

more polar: TLC: Rf 0.42, 0.37 (ethyl acetate:acetic acid=50:1); NMR: δ 7.19 (1H, dd, J=5.1 Hz, 1.2 Hz), 6.97 (1H, dd, J=5.1 Hz, 3.3 Hz), 6.92–6.85 (1H, m), 5.91–5.58 (2H, m), 4.58–4.32 (1H, m), 4.20–3.95 (1H, m), 3.43–2.15 (15H, m), 1.98–1.78 (2H, m).

Example 2(l)

11 α, 15-dihydroxy-9-oxo-16-(4-methoxy-3-chlorophenyl)-17,18,19,20-tetranor-3,7-dithiaprost-13E-enoic acid

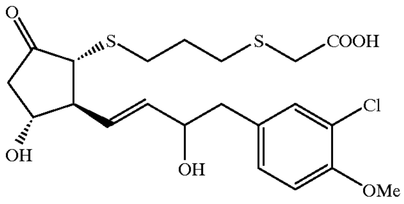

less polar: TLC: Rf 0.35, 0.29 (ethyl acetate:hexane:acetic acid=15:5:1); NMR: δ 7.23 (s, 1H), 7.08 (d, J=8 Hz, 1H), 6.89 (d, J=8 Hz, 1H), 5.80 and 5.77 (dd, J=15, 6 Hz, 1H), 5.67 and 5.59 (dd, J=15, 8 Hz, 1H), 4.4–4.3 and 4.1–4.0 (m, 2H), 4.0–3.4 (br, 3H), 3.89 (s, 3H), 3.22 (s, 3H), 3.39 and 3.0–2.2 (m, 10H), 1.9–1.8 (m, 2H).

more polar: TLC: Rf 0.33, 0.21 (ethyl acetate:hexane:acetic acid=15:5:1); NMR: δ 7.24 (d, J=2 Hz, 1H), 7.08 (dd, J=8, 2 Hz, 1H), 6.88 (d, J=8 Hz, 1H), 5.81 and 5.79 (dd, J=15, 5 Hz, 1H), 5.72 and 5.62 (dd, J=15, 8 Hz, 1H), 4.45–4.4 and 4.1–4.05 (m, 2H), 3.89 (s, 3H), 3.7–2.8 (br, 3H), 3.22 (s, 3H), 3.38 and 3.0–2.5 (m, 9H), 2.42 (dd, J=19, 10 Hz), 2.26 (dd, J=19, 7 Hz), 1.9–1.8 (m, 2H).

Example 2(m)

11 α, 15-dihydroxy-9-oxo-16-(3-trifluoromethylphenyl)-17,18,19,20-tetranor-3,7-dithiaprost-13E-enoic acid

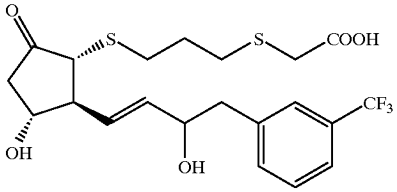

less polar: TLC: Rf 0.45, 0.41 (ethyl acetate:acetic acid=50:1); NMR: δ 7.58–7.38 (4H, m), 5.91–5.52 (2H, m), 4.53–3.96 (2H, m), 3.94–3.50 (3H, br), 3.44–2.16 (12H, m), 1.97–1.78 (2H, m).

more polar: TLC: Rf 0.37, 0.31 (ethyl acetate:acetic acid=50:1); NMR: δ 7.57–7.38 (4H, m), 5.91–5.57 (2H, m), 4.54–3.98 (2H, m), 3.46–2.14 (15H, m), 1.97–1.78 (2H, m).

Example 2(n)

11 α, 15-dihydroxy-9-oxo-16-(4-methoxymethylphenyl)-17,18,19,20-tetranor-3,7-dithiaprost-13E-enoic acid

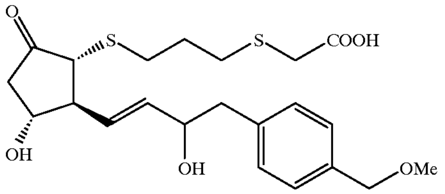

less polar: TLC: Rf 0.27, 0.20 (ethyl acetate:hexane:acetic acid=15:5:1); NMR: δ 7.35–7.15 (m, 4H), 5.9–5.5 (m, 2H), 4.5–4.4 (m, 3H), 4.3–4.2 and 4.05–3.9 (m, 1H), 3.42 (m, 3H), 3.22 (s, 2H), 3.7–2.7 (br, 3H), 3.4–3.3 and 3.0–2.2 (m, 10H), 2.0–1.8 (m, 2H).

more polar: TLC: Rf 0.24, 0.15 (ethyl acetate:hexane:acetic acid=15:5:1); NMR: δ 7.35–7.15 (m, 4H), 5.9–5.5 (m, 2H), 4.5–4.4 (m, 3H), 4.4–4.3 and 4.1–3.9 (m, 1H), 4.0–3.5 (br, 3H), 3.42 (m, 3H), 3.22 (s, 2H), 3.4–3.3 and 3.0–2.2 (m, 10H), 2.0–1.8 (m, 2H).

Example 2(o)

11 α, 15-dihydroxy-9-oxo-16-(3,4-dichlorophenyl)-17,18, 19,20-tetranor-3,7-dithiaprost-13E-enoic acid

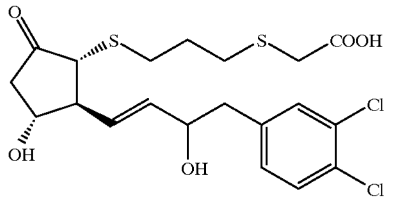

less polar: TLC: Rf 0.42, 0.38 (ethyl acetate:acetic acid=50:1); NMR: δ 7.44–7.30 (2H, m), 7.13–7.02 (1H, m), 5.90–5.54 (2H, m), 4.49–4.32 (1H, m), 4.19–4.00 (1H, m), 3.44–2.15 (15H, m), 1.98–1.80 (2H, m).

more polar: TLC: Rf 0.34, 0.28 (ethyl acetate:acetic acid=50:1); NMR: δ 7.38 (1H, d, J=8.4 Hz), 7.34 (1H, d, J=1.8 Hz), 7.07 (1H, dd, J=8.4 Hz, 1.8 Hz), 5.92–5.54 (2H, m), 4.53–4.32 (1H, m), 4.20–4.00 (1H, m), 3.44–2.12 (15H, m), 1.98–1.80 (2H, m).

Example 2(p)

11 α, 15-dihydroxy-9-oxo-16-(4-methylthiophenyl)-17,18, 19,20-tetranor-3,7-dithiaprost-13E-enoic acid

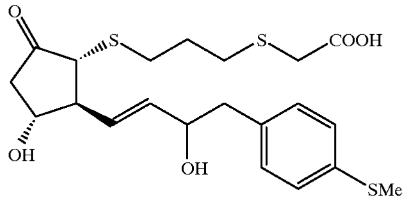

more polar: TLC: Rf 0.52, 0.41 (ethyl acetate:acetic acid=100:1); NMR: δ 7.22 (2H, d, J=8.6 Hz), 7.14 (2H, d, J=8.6 Hz), 5.90–5.54 (2H, m), 4.43 and 4.06 (2H, each m),3.22 (2H, s), 3.40–2.16 (13H, m), 2.47 (3H, s), 1.87 (2H, quintet, J=7.0 Hz).

Example 2(q)

11 α, 15-dihydroxy-9-oxo-16-(3-methylthiophenyl)-17,18, 19,20-tetranor-3,7-dithiaprost-13E-enoic acid

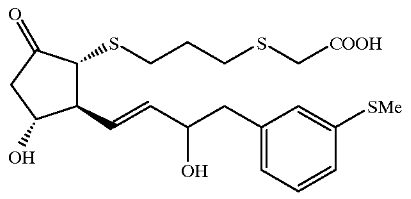

more polar: TLC: Rf 0.55, 0.41 (ethyl acetate:acetic acid=100:1); NMR: δ 7.24 (1H, m), 7.12 (2H, m), 6.99, (1H, m), 5.90–5.52 (2H, m), 4.43 and 4.03 (2H, each m), 3.80 (3H, br), 3.22 (2H, s), 3.40–2.09 (10H, m), 2.48 (3H, s), 1.87 (2H, quintet, J=7.0 Hz).

Example 2(r)

11 α, 15-dihydroxy-9-oxo-16-(biphenyl-3-yl)-17,18,19,20-tetranor-3,7-dithiaprost-13E-enoic acid

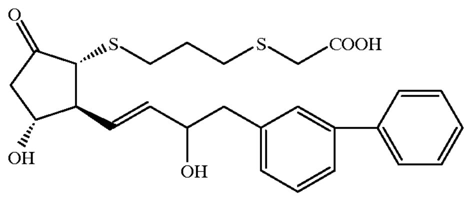

less polar: TLC: Rf 0.41, 0.34 (ethyl acetate:acetic acid=50:1); NMR: δ 7.66–7.14 (9H, m), 5.92–5.50 (2H, m), 4.60–3.85 (2H, m), 3.40–2.10 (15H, m), 1.96–1.75 (2H, m).

more polar: TLC: Rf 0.34, 0.28 (ethyl acetate:acetic acid=50:1); NMR: δ 7.64–7.14 (9H, m), 5.95–5.57 (2H, m), 4.64–3.92 (2H, m), 3.40–2.08 (15H, m), 1.96–1.74 (2H, m).

Example 2(s)

11 α, 15-dihydroxy-9-oxo-16-(3-ethylphenyl)-17,18,19,20-tetranor-3,7-dithiaprost-13E-enoic acid

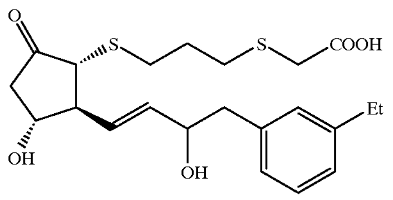

less polar:: TLC: Rf 0.46, 0.42 (ethyl acetate:acetic acid=50:1); NMR: δ 7.34–6.95 (4H, m), 5.90–5.47 (2H, m), 4.58–3.84 (2H, m), 3.42–2.10 (17H, m), 2.00–1.78 (2H, m), 1.32–1.16 (3H, m).

more polar: TLC: Rf 0.42, 0.36 (ethyl acetate:acetic acid=50:1); NMR: δ 7.30–6.96 (4H, m), 5.90–5.55 (2H, m), 4.43–4.30 (1H, m), 4.14–3.96 (1H, m), 3.90–3.41 (3H, br), 3.41–2.16 (14H, m), 1.96–1.78 (2H, m), 1.23 (3H, t, J=7.5 Hz).

Example 2(t)

11 α, 15-dihydroxy-9-oxo-16-(3,5-dimethylphenyl)-17,18, 19,20-tetranor-3,7-dithiaprost-13E-enoic acid

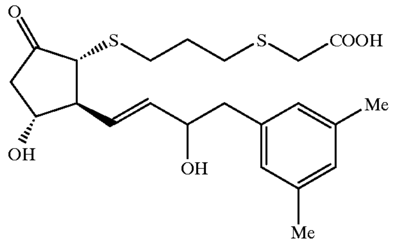

less polar: TLC: Rf 0.52, 0.45 (ethyl acetate:acetic acid=50:1); NMR: δ 6.88 (1H, brs), 6.82 (2H, brs), 5.88–5.45 (2H, m), 4.52–3.75 (5H, m), 3.42–2.31 (12H, m), 2.29 (6H, s), 2.00–1.78 (2H, m).

more polar: TLC: Rf 0.50, 0.45 (ethyl acetate:acetic acid=50:1); NMR: δ 6.88 (1H, brs), 6.83 (2H, brs), 5.91–5.58 (2H, m), 4.55–4.30 (1H, m), 4.16–3.96 (1H, m), 3.42–2.32 (15H, m), 2.29 (6H, s), 1.99–1.78 (2H, m).

Example 2(u)

11 α, 15-dihydroxy-9-oxo-16-(3-methoxymethylphenyl)-17,18,19,20-tetranor-3,7-dithiaprost-13E-enoic acid

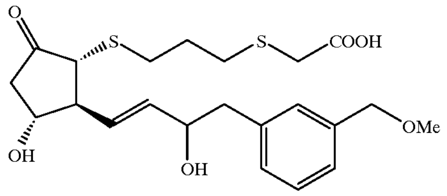

less polar: TLC: Rf 0.22, 0.16 (ethyl acetate:hexane:acetic acid=15:5:1); NMR: δ 7.35–7.1 (m, 4H), 5.85–5.3 (m, 2H), 4.5–4.35 (m, 3H), 4.3–4.15 and 3.95–3.8 (m, 1H), 3.42 and 3.41 (s, 3H), 3.7–3.0 (br, 3H), 3.22 (s, 2H), 3.4–3.3 and 3.1–2.2 (m, 10H), 2.0–1.8 (m, 2H).

Example 2(v)

11 α, 15-dihydroxy-9-oxo-16-(2-methoxy-3-methylphenyl)-17,18,19,20-tetranor-3,7-dithiaprost-13E-enoic acid

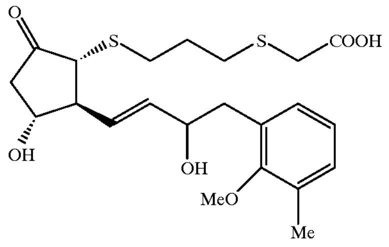

less polar: TLC: Rf 0.59, 0.54 (ethyl acetate:acetic acid=19:1); NMR: δ 7.15–7.0 (m, 3H), 5.85–5.2 (m, 2H), 4.5–4.4 (m, 1H), 4.3–4.2 and 3.9–3.8 (m, 1H), 4.1–3.4 (br, 3H), 3.78 and 3.77 (s, 3H), 3.22 (s, 2H), 3.35–3.3 and 3.0–2.4 (m, 10H), 2.30 (s, 3H), 1.95–1.8 (m, 2H).

more polar: TLC: Rf 0.56, 0.45 (ethyl acetate:acetic acid=19:1); NMR: δ 7.2–7.0 (m, 3H), 5.76 (dd, J=16, 5 Hz, 1H), 5.52 (dd, J=16, 8 Hz, 1H), 4.7–4.5 (m, 1H), 4.3–4.2 and 4.0–3.8 (m, 1H), 4.4–3.4 (br, 3H), 3.78 and 3.77 (s, 3H), 3.22 (s, 2H), 3.3–3.2 and 3.1–2.3 (m, 10H), 2.30 (s, 3H), 1.95–1.8 (m, 2H).

Example 2(w)

11 α, 15-dihydroxy-9-oxo-16-(4-mesylphenyl)-17,18,19,20-tetranor-3,7-dithiaprost-13E-enoic acid

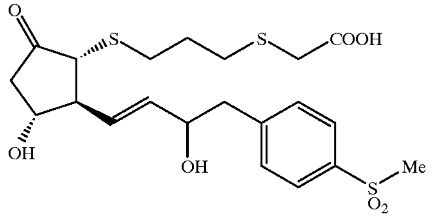

more polar: TLC: Rf 0.18, 0.14 (ethyl acetate:acetic acid=20:1); NMR ($CD_3OD$): δ 7.86 (2H, m), 7.52 (2H, m), 5.69 (2H, m), 4.36 and 4.05 (2H, each m), 3.52–2.08 (10H, m), 3.23 (2H, s), 3.10 (3H, s), 1.86 (2H, m).

Example 2(x)

11 α, 15-dihydroxy-9-oxo-16-(2,3-dimethylphenyl)-17,18,19,20-tetranor-3,7-dithiaprost-13E-enoic acid

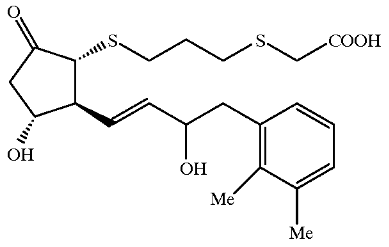

less polar: TLC: Rf 0.66, 0.60 (ethyl acetate:acetic acid=19:1); NMR: δ 7.1–7.0 (m, 3H), 5.9–5.4 (m, 2H), 4.5–4.4 (m, 1H), 4.3–4.2 and 4.0–3.85 (m, 1H), 3.8–3.0 (br, 3H), 3.22 (s, 2H), 3.4–3.35 and 3.0–2.3 (m, 10H), 2.28 (s, 3H), 2.24 (s, 3H), 2.0–1.8 (m, 2H).

more polar: TLC: Rf 0.62, 0.5:1 (ethyl acetate:acetic acid=19:1); NMR: δ 7.1–7.0 (m, 3H), 5.9–5.6 (m, 2H), 4.5–4.4 (m, 1H), 4.2–4.0 (m, 1H), 3.8–3.0 (br, 3H), 3.22 (s, 2H), 3.4–3.35 and 3.0–2.3 (m, 10H), 2.28 (s, 3H), 2.24 (s, 3H), 2.0–1.8 (m, 2H).

Example 2(y)

11 α, 15-dihydroxy-9-oxo-16-(4-ethoxyphenyl)-17,18,19,20-tetranor-3,7-dithiaprost-13E-enoic acid

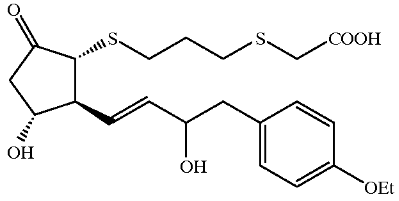

less polar: TLC: Rf 0.49, 0.42 (ethyl acetate:acetic acid=50:1); NMR: δ 7.12 (2H, d, J=8.8 Hz), 6.85 (2H, d, J=8.8 Hz), 5.86–5.49 (2H, m), 4.46–4.24 (1H, m), 4.05–3.92 (1H, m), 4.01 (2H, q, J=7.0 Hz), 3.85–3.10 (3H, br), 3.40–2.20 (10H, m), 3.22 (2H, s), 1.95–1.80 (2H, m), 1.41 (3H, t, J=7.0 Hz).

more polar: TLC: Rf 0.41, 0.30 (ethyl acetate:acetic acid=50:1); NMR: δ 7.12 (2H, d, J=8.8 Hz), 6.84 (2H, d, J=8.8 Hz), 5.87–5.54 (2H, m), 4.46–4.32 (1H, m), 4.40–3.65 (4H, br), 4.01 (2H, q, J=7.0 Hz), 3.39–2.20 (10H, m), 3.22 (2H, s), 1.94–1.80 2H, m), 1.40 (3H, t, J=7.0 Hz).

Example 2(z)

11 α, 15-dihydroxy-9-oxo-16-(3-ethoxyphenyl)-17,18,19,20-tetranor-3,7-dithiaprost-13E-enoic acid

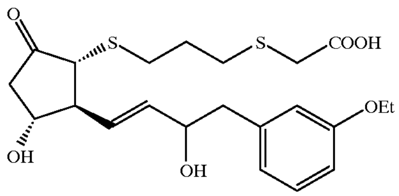

less polar: TLC: Rf 0.46, 0.36 (ethyl acetate:acetic acid=50:1); NMR: δ 7.27–7.18 (1H, m), 6.80–6.76 (3H, m), 5.85–5.45 (2H, m), 4.60–4.00 (4H, br), 4.07–3.90 (1H, m), 4.03 (2H, q, J=7.0 Hz), 3.38–2.08 (10H, m), 3.22 (2H, s), 1.94–1.79 (2H, m), 1.41 (3H, t, J=7.0 Hz).

more polar: TLC: Rf 0.41, 0.31 (ethyl acetate:acetic acid=50:1); NMR: δ 7.27–7.17 (1H, m), 6.80–6.76 (3H, m), 5.87–5.53 (2H, m), 4.80–4.40 (4H, br), 4.14–4.00 (1H, m), 4.02 (2H, q, J=7.0 Hz), 3.38–2.18 (10H, m), 3.22 (2H, s), 1.92–1.78 (2H, m), 1.41 (3H, t, J=7.0 Hz).

Example 2(aa)

11 α, 15-dihydroxy-9-oxo-16-(2-naphthyl)-17,18,19,20-tetranor-3,7-dithiaprost-13E-enoic acid

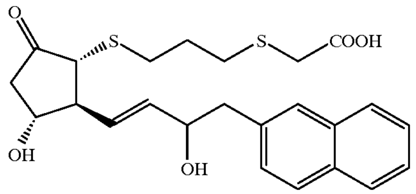

less polar: TLC: Rf 0.19, 0.14 (ethyl acetate:acetic acid=50:1); NMR: δ 7.88–7.30 (7H, m), 5.96–5.44 (2H, m), 4.64–3.82 (2H, m), 3.40–2.00 (15H, m), 2.00–1.74 (2H, m).

more polar: TLC: Rf 0.18, 0.13 (ethyl acetate:acetic acid=50:1); NMR: δ 7.87–7.28 (7H, m), 5.96–5.46 (2H, m), 4.66–3.88 (2H, m), 3.60–2.10 (15H, m), 1.92–1.70 (2H, m).

Example 2(bb)

11 α, 15-dihydroxy-9-oxo-16-(3,4-dimethoxyphenyl)-17,18,19,20-tetranor-3,7-dithiaprost-13E-enoic acid

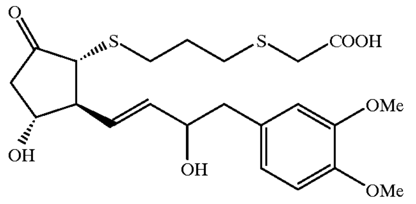

less polar: TLC: Rf 0.20, 0.16 (ethyl acetate:acetic acid=50:1); NMR: δ 6.88–6.70 (3H, m), 5.90–5.45 (2H, m), 4.49–3.94 (2H, m), 3.88 (3H, s), 3.86 (3H, s), 3.42–2.12 (15H, m), 1.98–1.76 (2H, m).

more polar: TLC: Rf 0.16, 0.11 (ethyl acetate:acetic acid=50:1); NMR: δ 6.88–6.72 (3H, m), 5.93–5.58 (2H, m), 4.54–4.00 (2H, m), 3.88 (3H, s), 3.86 (3H, s), 3.60–2.16 (15H, m), 1.98–1.78 (2H, m).

Example 2(cc)

11 α, 15-dihydroxy-9-oxo-16-(3-methyl-4-methoxyphenyl)-17,18,19,20-tetranor-3,7-dithiaprost-13E-enoic acid

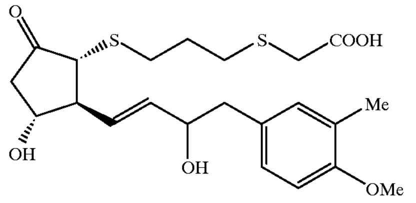

less polar: TLC: Rf 0.50, 0.42 (ethyl acetate:acetic acid=50:1); NMR: δ 6.99 (2H, m), 6.77 (1H, d, J=9.0 Hz), 5.88–5.48 (2H, m), 4.34 and 3.98 (2H, each m), 3.81 (3H, s), 3.78 (3H, br), 3.21 (2H, s), 3.40–2.23 (10H, m), 2.20 (3H, s), 1.87 (2H, m).

more polar: TLC: Rf 0.47, 0.32 (ethyl acetate:acetic acid=50:1); NMR: δ 6.99 (2H, m), 6.76 (1H, d, J=9.0 Hz), 5.90–5.55 (2H, m), 4.40 and 4.06 (2H, each m), 4.03 (3H, br), 3.81 (3H, s), 3.21 (2H, s), 3.41–2.27 (10H, m), 2.20 (3H, s), 1.88 (2H, m).

Example 2(dd)

11 α, 15-dihydroxy-9-oxo-16-(3-isopropylphenyl)-17,18,19,20-tetranor-3,7-dithiaprost-13E-enoic acid

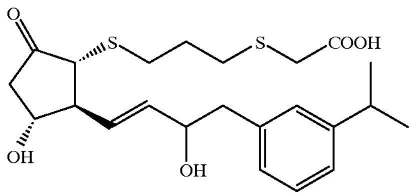

less polar: TLC: Rf 0.40, 0.30 (ethyl acetate:hexane:acetic acid=15:5:1); NMR: δ 7.3–7.0 (m, 4H), 5.9–5.5 (m, 2H), 4.5–4.4 (m, 1H), 4.3–4.2 and 4.0–3.9 (m,1H), 4.1–3.5 (br, 3H), 3.22 (s, 2H), 3.4–3.3 and 3.0–2.2 (m, 11H), 2.0–1.8 (m, 2H), 1.24 (d, J=7 Hz, 6H).

more polar: TLC: Rf 0.35, 0.25 (ethyl acetate:hexane:acetic acid=15:5:1); NMR: δ 7.3–7.0 (m, 4H), 5.9–5.6 (m, 2H), 4.55–4.4 and 4.2–4.0 (m, 2H), 4.2–3.8 (br, 3H), 3.22 (s, 2H), 3.4–3.3 and 3.0–2.2 (m, 11H), 2.0–1.8 (m, 2H), 1.24 (d, J=7 Hz, 6H).

Example 2(ee)

11 α, 15-dihydroxy-9-oxo-16-(2,5-dimethylphenyl)-17,18,19,20-tetranor-3,7-dithiaprost-13E-enoic acid

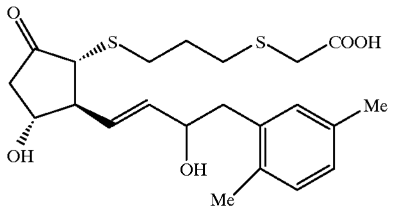

less polar: TLC: Rf 0.39, 0.29 (ethyl acetate:acetic acid=50:1); NMR: δ 7.12–6.92 (3H, m), 5.92–5.44 (2H, m), 4.56–3.50 (5H, m), 3.41–2.14 (18H, m), 1.98–1.78 (2H, m).

more polar: TLC: Rf 0.29, 0.19 (ethyl acetate:acetic acid=50:1); NMR: δ 7.12–6.88 (3H, m), 5.93–5.56 (2H, m), 4.52–3.80 (5H, m), 3.42–2.14 (18H, m), 1.98–1.78 (2H, m).

Example 2(ff)

11 α, 15-dihydroxy-9-oxo-16-(2-methoxy-5-chlorophenyl)-17,18,19,20-tetranor-3,7-dithiaprost-13E-enoic acid

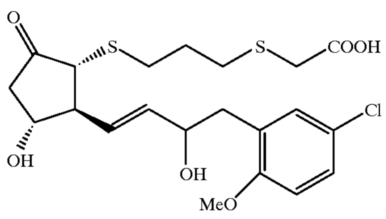

less polar: TLC: Rf 0.52, 0.44 (ethyl acetate:acetic acid=50:1); NMR: δ 7.17 (2H, m), 6.82 (1H, d, J=8.4 Hz), 5.88–5.47 (2H, m), 4.56–3.94 (2H, m), 3.84 (3H, s), 3.49 (3H, br), 3.21 (2H, s), 3.40–2.15 (10H, m), 1.88 (2H, m).

more polar: TLC: Rf 0.46, 0.34 (ethyl acetate:acetic acid=50:1); NMR: δ 7.17 (2H, m), 6.82 (1H, d, J=8.8 Hz), 5.87–5.54 (2H, m), 4.62–3.95 (2H, m), 3.84 (3H, s), 3.50 (3H, br), 3.22 (2H, s), 3.37–2.17 (10H, m), 1.87 (2H, m).

Example 2(gg)

11 α, 15-dihydroxy-9-oxo-16-(5-methoxy-3-methylphenyl)-17,18,19,20-tetranor-3,7-dithiaprost-13E-enoic acid

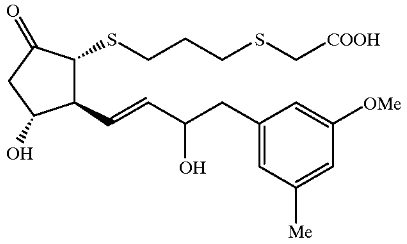

less polar: TLC: Rf 0.26, 0.18 (ethyl acetate:hexane:acetic acid=15:5:1); NMR: δ 6.65–6.55 (m, 3H), 5.9–5.5 (m, 2H), 4.5–4.4 (m, 1H), 4.4–4.3 and 4.05–3.9 (m, 1H), 3.79 (s, 3H), 3.22 (s, 2H), 3.4–2.6 (br, 3H), 3.4–3.3 and 3.0–2.4 (m, 10H), 2.32 (s, 3H), 2.0–1.8 (m, 2H).

more polar: TLC: Rf 0.23, 0.11 (ethyl acetate:hexane:acetic acid=15:5:1); NMR: δ 6.65–6.55 (m, 3H), 5.9–5.6 (m, 2H), 4.5–4.3 and 4.1–4.0 (m, 2H), 3.79 (s, 3H), 3.7–3.0 (br, 3H), 3.22 (s, 2H), 3.4–3.3 and 3.0–2.3 (m, 10H), 2.32 (s, 3H), 2.0–1.8 (m, 2H).

Example 2(hh)

11 α, 15-dihydroxy-9-oxo-16-(3-propylphenyl)-17,18,19,20-tetranor-3,7-dithiaprost-13E-enoic acid

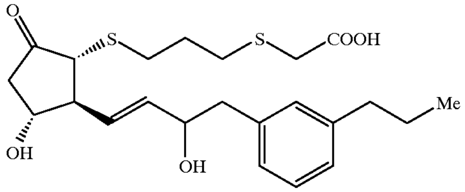

less polar: TLC: Rf 0.70, 0.62 (ethyl acetate:acetic acid=20:1); NMR: δ 7.3–7.0 (m, 4H), 5.9–5.5 (m, 2H), 4.5–4.4 (m, 1H), 4.3–4.2 and 4.0–3.9 (m, 1H), 3.8–2.8 (br, 3H), 3.22 (s, 2H), 3.4–3.3 and 3.0–2.2 (m, 12H), 2.0–1.8 (m, 2H), 1.75–1.55 (m, 2H), 0.94 (t, J=7 Hz, 3H).

more polar: TLC: Rf 0.68, 0.58 (ethyl acetate:acetic acid=20:1); NMR: δ 7.3–7.0 (m, 4H), 5.9–5.6 (m, 2H), 4.55–4.3 and 4.1–4.0 (m, 1H), 3.6–3.0 (br, 3H), 3.22 (s, 2H), 3.4–3.3 and 3.0–2.2 (m, 12H), 2.0–1.8 (m, 2H), 1.75–1.55 (m, 2H), 0.94 (t, J=7 Hz, 3H).

Example 2(ii)

11 α, 15-dihydroxy-9-oxo-16-[3-(2-furyl)phenyl]-17,18,19,20-tetranor-3,7-dithiaprost-13E-enoic acid

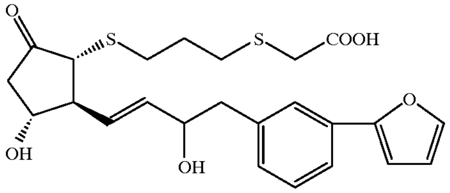

less polar: TLC: Rf 0.56, 0.49 (ethyl acetate:acetic acid=50:1); NMR: δ 7.55 (2H, m), 7.47 (1H, d, J=1.7 Hz), 7.33 (1H, m), 7.11 (1H, m), 6.67 (1H, d, J=3.3 Hz), 6.48 (1H, dd, J=3.3, 1.7 Hz), 5.90–5.47 (2H, m), 4.56–3.88 (2H, m), 3.67 (3H, br), 3.21 (2H, s), 3.39–2.13 (10H, m), 1.87 (2H, m).

more polar: TLC: Rf 0.53, 0.44 (ethyl acetate:acetic acid=50:1); NMR: δ 7.54 (2H, m), 7.47 (1H, d, J=1.9 Hz), 7.32 (1H, t, J=7.9 Hz), 7.10 (1H, d, J=7.9 Hz), 6.66 (1H, d, J=3.4 Hz), 6.47 (1H, dd, J=3.4, 1.9 Hz), 5.91–5.53 (2H, m), 4.56–3.94 (2H, m), 3.78 (3H, br), 3.21 (2H, s), 3.39–2.13 (10H, m), 1.84 (2H, m).

Example 2(jj)

11 α, 15-dihydroxy-9-oxo-16-(3-mesylphenyl)-17,18,19,20-tetranor-3,7-dithiaprost-13E-enoic acid

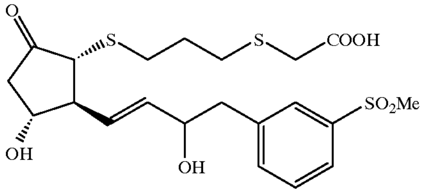

less polar: TLC: Rf 0.1 4, 0.20 (chloroform:methanol:acetic acid=90:10:1); NMR ($CD_3OD$): δ 7.87–7.75 (2H, m), 7.66–7.50 (2H, m), 5.86–5.55 (2H, m), 4.42–3.99 (2H, m), 3.70–2.10 (10H, m), 3.23 (2H, s), 3.12 (3H, s), 1.92–1.77 (2H, m).

more polar: TLC: Rf 0.1 2, 0.18 (chloroform:methanol:acetic acid=90:10:1); NMR ($CD_3OD$): δ 7.85–7.76 (2H, m), 7.64–7.50 (2H, m), 5.83–5.50 (2H, m), 4.43–3.99 (2H, m), 3.49–2.12 (10H, m), 3.22 (2H, s), 3.12 (3H, s), 1.93–1.78 (2H, m).

Example 2(kk)

11 α, 15-dihydroxy-9-oxo-16-(5-methoxymethylthiophen-2-yl)-17,18,19,20-tetranor-3,7-dithiaprost-13E-enoic acid

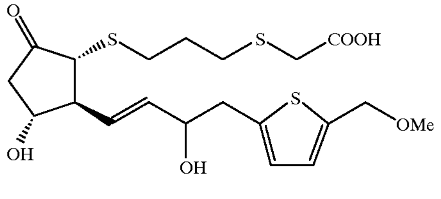

less polar: TLC: Rf 0.45, 0.36 (ethyl acetate:acetic acid=20:1); NMR: δ 6.85 (d, J=3 Hz, 1H), 6.74 (d, J=3 Hz, 1H), 5.9–5.5 (m, 2H), 4.55 (s, 2H), 4.5–4.3 and 4.1–3.9 (m, 2H), 4.2–3.5 (br, 3H), 3.40 (s, 3H), 3.22 (s, 2H), 3.4–3.35 and 3.1–2.2 (m, 10H), 2.0–1.8 (m, 2H).

more polar: TLC: Rf 0.42, 0.29 (ethyl acetate:acetic acid=20:1); NMR: δ 6.85 (d, J=3 Hz, 1H), 6.74 (d, J=3 Hz, 1H), 5.9–5.6 (m, 2H), 4.55 (s, 2H), 4.55–4.35 and 4.1–3.9 (m, 2H), 4.3–3.5 (br, 3H), 3.40 (s, 3H), 3.22 (s, 2H), 3.4–3.35 and 3.1–2.3 (m, 10H), 2.0–1.8 (m, 2H).

Example 2(ll)

11 α, 15-dihydroxy-9-oxo-16-(5-phthalanyl)-17,18,19,20-tetranor-3,7-dithiaprost-13E-enoic acid

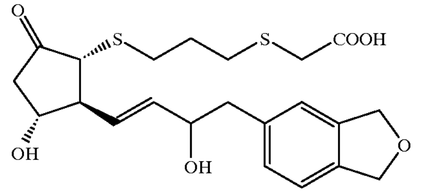

less polar: TLC: Rf 0.32, 0.23 (ethyl acetate:acetic acid=50:1); NMR ($CD_3OD$): δ 7.17 (3H, m), 5.76 (1H, dd, J=15, 5.6 Hz), 5.63 (1H, dd, J=15, 7.1 Hz), 5.04 (4H, s), 4.30 and 4.03 (2H, each m), 3.22 (2H, s), 3.52–2.16 (10H, m), 1.84 (2H, m).

more polar: TLC: Rf 0.25, 0.14 (ethyl acetate:acetic acid=50:1); NMR ($CD_3OD$): δ 7.16 (3H, m), 5.73 (1H, dd, J=15, 6.3 Hz), 5.58 (1H, dd, J=15, 7.6 Hz), 5.04 (4H, s), 4.30 and 4.04 (2H, each m), 3.21 (2H, s), 3.50–2.16 (10H, m), 1.82 (2H, m).

Example 2(mm)

11 α, 15-dihydroxy-9-oxo-16-(3-ethyoxymethylphenyl)-17,18,19,20-tetranor-3,7-dithiaprost-13E-enoic acid

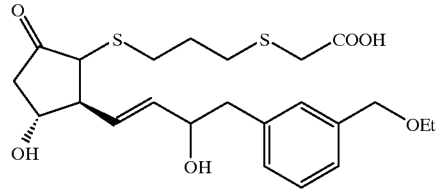

less polar: TLC: Rf 0.29, 0.23 (ethyl acetate:acetic acid=50:1); NMR: δ 7.36–7.10 (4H, m), 5.86–5.30 (2H, m), 4.56–3.37 (9H, m), 3.37–2.10 (12H, m), 1.98–1.76 (2H, m), 1.25 (3H, t, J=7.1 Hz).

more polar: TLC: Rf 0.23, 0.14 (ethyl acetate:acetic acid=50:1); NMR: δ 7.35–7.10 (4H, m), 5.91–5.47 (2H, m), 4.60–3.50 (9H, m), 3.38–2.10 (12H, m), 1.96–1.76 (2H, m), 1.25 (3H, t, J=6.9 Hz).

Example 2(nn)

11 α, 15-dihydroxy-9-oxo-16-(3-methylthiomethylphenyl)-17,18,19,20-tetranor-3,7-dithiaprost-13E-enoic acid

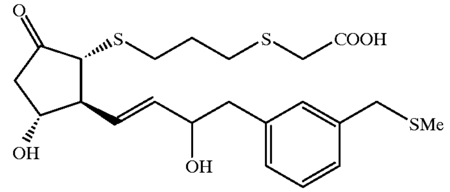

less polar: TLC: Rf 0.31, 0.27 (ethyl acetate:acetic acid=50:1); NMR: δ 7.34–7.05 (4H, m), 5.88–5.45 (2H, m), 4.55–3.88 (2H, m), 3.88–2.10 (17H, m), 2.03 (3H, s), 1.98–1.78 (2H, m).

more polar: TLC: Rf 0.27, 0.19 (ethyl acetate:acetic acid=50:1); NMR: δ 7.35–7.05 (4H, m), 5.92–5.56 (2H, m), 4.58–3.96 (2H, m), 3.88–2.10 (17H, m), 2.04–2.02 (3H, m), 1.98–1.78 (2H, m).

Example 2(oo)

11 α, 15-dihydroxy-9-oxo-16-(3-hydroxymethylphenyl)-17,18,19,20-tetranor-3,7-dithiaprost-13E-enoic acid

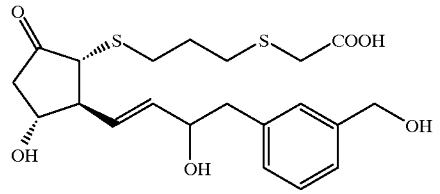

less polar: TLC: Rf 0.39, 0.33 (chloroform:methanol:acetic acid=90:10:1); NMR ($CD_3OD$): δ 7.32–7.09 (4H, m), 5.77 (1H, dd, J=16, 5.6 Hz), 5.60 (1H, dd, J=16, 7.6 Hz), 4.58 (2H, s), 4.28 and 4.02 (2H, each m), 3.22 (2H, s), 3.54–2.05 (10H, m), 1.84 (2H, m).

more polar: TLC: Rf 0.37, 0.30 (chloroform:methanol:acetic acid=90:10:1); NMR ($CD_3OD$): δ 7.31–7.09 (4H, m), 5.75 (1H, dd, J=15, 6.2 Hz), 5.59 (1H, dd, J=15, 7.3 Hz), 4.58 (2H, s), 4.32 and 4.02 (2H, each m), 3.22 (2H, s), 3.49–2.08 (10H, m), 1.82 (2H, m).

Example 2(pp)

11 α, 15-dihydroxy-9-oxo-16-[3-(2-methoxyethyl)phenyl]-17,18,19,20-tetranor-3,7-dithiaprost-13E-enoic acid

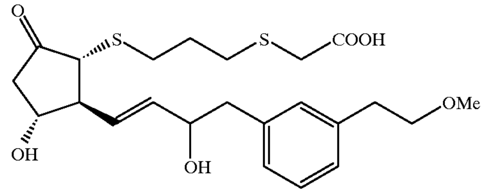

less polar: TLC: Rf 0.36, 0.25 (ethyl acetate:acetic acid=50:1); NMR: δ 7.30–7.00 (4H, m), 5.80 (1H, dd, J=15.4, 6.2 Hz), 5.66, 5.54 (1H, dd, J=15.4, 8.0 Hz), 5.30–4.50 (3H, br), 4.50–4.34 (1H, m), 4.30–3.87 (1H, m), 3.65 (2H, t, J=6.6 Hz), 3.35 (3H, s), 3.21 (2H, s), 2.98–2.14 (12H, m), 1.93–1.80 (2H, m).

more polar: TLC: Rf 0.31, 0.17 (ethyl acetate:acetic acid=50:1); NMR: δ 7.30–7.01 (4H, m), 5.80 (1H, dd, J=15.4, 5.8 Hz), 5.60 (1H, dd, J=15.4, 8.0 Hz), 5.50–4.60 (3H, br), 4.47–4.28 (1H, m), 4.06–3.96 (1H, m), 3.65 (2H, t, J=6.6 Hz), 3.35 (3H, s), 3.21 (2H, s), 3.00–2.18 (12H, m), 1.93–1.80 (2H, m).

Example 2(qq)

11 α, 15-dihydroxy-9-oxo-16-[3-(1-methoxyethyl)phenyl]-17,18,19,20-tetranor-3,7-dithiaprost-13E-enoic acid

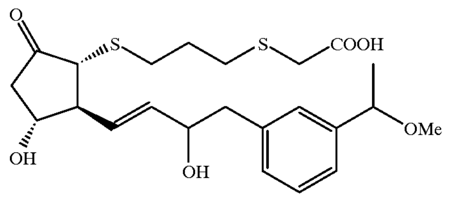

less polar: TLC: Rf 0.50, 0.40 (ethyl acetate:acetic acid=20:1); NMR: δ 7.35–7.1 (m, 4H), 5.9–5.4 (m, 2H), 4.5–4.4 (m, 1H), 4.4–4.2 (m, 1H), 4.1–3.8 (m, 1H), 4.2–3.5 (br, 3H), 3.27 and 3.26 (s, 3H), 3.22 (s, 2H), 3.4–3.35 and 3.0–2.3 (m, 8H), 2.0–1.8 (m, 2H), 1.45 (d, J=7 Hz, 3H).

more polar: TLC: Rf 0.43, 0.27 (ethyl acetate:acetic acid=20:1); NMR: δ 7.35–7.1 (m, 4H), 5.9–5.5 (m, 2H), 4.65–4.45 (m, 1H), 4.4–4.25 (m, 1H), 4.1–3.9 (m, 1H), 4.2–3.4 (br, 3H), 3.27 and 3.26 (s, 3H), 3.22 (s, 2H), 3.4–3.3 and 3.05–2.3 (m, 8H), 2.0–1.8 (m, 2H), 1.45 (d, J=7 Hz, 3H).

Example 2(rr)

11 α, 15-dihydroxy-9-oxo-16-(3-phenyloxymethylphenyl)-17,18,19,20-tetranor-3,7-dithiaprost-13E-enoic acid

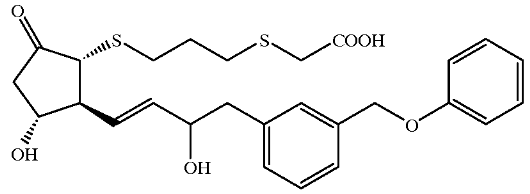

less polar: TLC: Rf 0.55, 0.43 (ethyl acetate:acetic acid=50:1); NMR: δ 7.40–7.14 (6H, m), 6.98 (3H, m), 5.86–5.41 (2H, m), 5.04 (2H, s), 4.53–3.78 (2H, m), 3.87 (3H, br), 3.21 (2H, s), 3.38–2.08 (10H, m), 1.85 (2H, m).

more polar: TLC: Rf 0.49, 0.32 (ethyl acetate:acetic acid=50:1); NMR: δ 7.38–7.13 (6H, m), 6.97 (3H, m), 5.88–5.52 (2H, m), 5.03 (2H, s), 4.53–3.90 (2H, m), 4.36 (3H, br), 3.20 (2H, s), 3.38–2.12 (10H, m), 1.85 (2H, m).

Example 2(ss)

11 α, 15-dihydroxy-9-oxo-16-(3-isopropyloxymethylphenyl)-17,18,19,20-tetranor-3,7-dithiaprost-13E-enoic acid

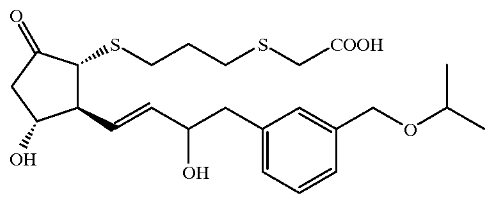

less polar: TLC: Rf 0.33, 0.24 (ethyl acetate:hexane:acetic acid=15:5:1); NMR: δ 7.3–7.1 (m, 4H), 5.85–5.3 (m, 2H), 4.55–4.35 (m, 3H), 4.25–4.1 and 3.9–3.7 (m, 2H), 3.7–3.0 (br, 3H), 3.22 (s, 2H), 3.4–3.3 and 3.1–2.2 (m, 10H), 2.0–1.8 (m, 2H), 1.3–1.2 (m, 6H).

more polar: TLC: Rf 0.29, 0.1 7 (ethyl acetate:hexane:acetic acid=15:5:1); NMR: δ 7.3–7.1 (m, 4H), 5.9–5.5 (m, 2H), 4.6–4.4 (m, 3H), 4.4–4.25 and 4.0–3.9 (m, 1H), 3.85–3.65 (m, 1H), 3.6–3.2 (br, 3H), 3.22 (s, 2H), 3.4–3.3 and 3.0–2.2 (m, 10H), 2.0–1.8 (m, 2H), 1.3–1.2 (m, 6H).

Example 2(tt)

11 α, 15-dihydroxy-9-oxo-16-[3-(2-fluoroethyl)phenyl]-17,18,19,20-tetranor-3,7-dithiaprost-13E-enoic acid

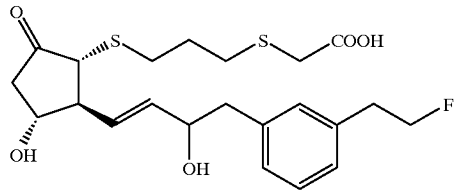

less polar: TLC: Rf 0.60, 0.52 (ethyl acetate:acetic acid=50:1); NMR: δ 7.32–7.04 (4H, m), 5.85–5.50 (2H, m), 4.80–4.30 (3H, br), 4.64 (2H, dt, J=47.2, 6.4 Hz), 4.50–4.38 (1H, m), 4.35–3.89 (1H, m), 3.21 (2H, s), 3.10–2.15 (12H, m), 1.95–1.79 (2H, m).

more polar: TLC: Rf 0.55, 0.43 (ethyl acetate:acetic acid=50:1); NMR: δ 7.32–7.04 (4H, m), 5.79 (1H, dd, J=15.4, 6.2 Hz), 5.59 (1H, dd, J=15.4, 8.2 Hz), 5.50–4.90 (3H, br), 4.62 (2H, dt, J=47.0, 6.4 Hz), 4.47–4.29 (1H, m), 4.10–3.96 (1H, m), 3.21 (2H, s), 3.07–2.20 (12H, m), 1.92–1.79 (2H, m).

Example 2(uu)

11 α, 15-dihydroxy-9-oxo-16-[3-(2-thienyl)phenyl]-17,18,19,20-tetranor-3,7-dithiaprost-13E-enoic acid

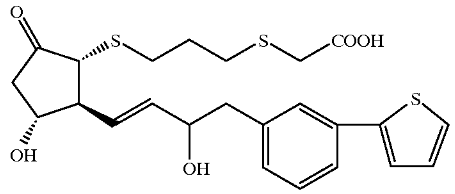

less polar: TLC: Rf 0.37, 0.31 (ethyl acetate:acetic acid=50:1); NMR: δ 7.56–7.40 (2H, m), 7.40–7.24 (3H, m), 7.18–7.02 (2H, m), 5.90–5.56 (2H, m), 4.54–3.64 (5H, m), 3.40–2.07 (12H, m), 1.95–1.74 (2H, m).

more polar: TLC: Rf 0.35, 0.27 (ethyl acetate:acetic acid=50:1); NMR: δ 7.55–7.40 (2H, m), 7.36–7.22 (3H, m), 7.15–7.02 (2H, m), 5.88–5.69 (1H, m), 5.56 (1H, dd, J=15.4 Hz, 8.0 Hz), 5.14–4.55 (3H, br), 4.50–4.27 (1H, m), 4.09–3.90 (1H, m), 3.37–2.12 (12H, m), 1.92–1.70 (2H, m).

Example 2(vv)

11 α, 15-dihydroxy-9-oxo-16-[3-(1-propynyl)phenyl]-17,18,19,20-tetranor-3,7-dithiaprost-13E-enoic acid

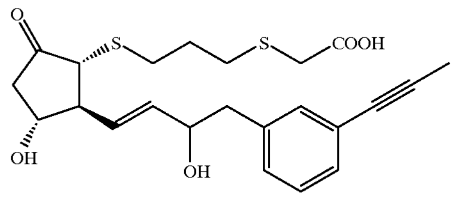

less polar: TLC: Rf 0.55, 0.45 (ethyl acetate:hexane=20:1); NMR: δ 7.3–7.1 (m, 4H), 5.85–5.4 (m, 2H), 4.5–4.35 (m, 1H), 4.35–4.2 and 4.05–3.9 (m, 1H), 4.2–3.4 (br, 3H), 3.22 (s, 2H), 3.4–3.3 and 3.0–2.2 (m, 10H), 2.04 (s, 3H), 2.0–1.8 (m, 2H).

more polar: TLC: Rf 0.49, 0.36 (ethyl acetate:hexane=20:1); NMR: δ 7.3–7.1 (m, 4H), 5.9–5.5 (m, 2H), 4.5–4.35 and 4.1–4.0 (m, 2H), 3.9–3.2 (br, 3H), 3.22 (s, 2H), 3.4–3.3 and 3.0–2.3 (m, 10H), 2.04 (s, 3H), 2.0–1.8 (m, 2H).

Example 2(ww)

11 α, 15-dihydroxy-9-oxo-16-(3-benzylphenyl)-17,18,19, 20-tetranor-3,7-dithiaprost-13E-enoic acid

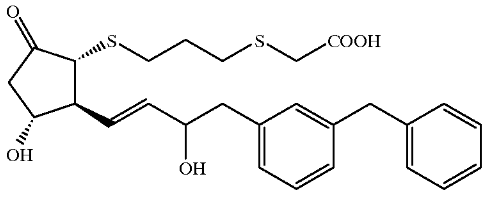

less polar: TLC: Rf 0.59, 0.48 (ethyl acetate:acetic acid=50:1); NMR: δ 7.36–6.99 (9H, m), 5.82–5.39 (2H, m), 4.5:1–3.72 (2H, m), 3.96 (2H, s), 3.53 (3H, br), 3.20 (2H, s), 3.38–2.08 (10H, m), 1.88 (2H, m).

more polar: TLC: Rf 0.50, 0.36 (ethyl acetate:acetic acid=50:1); NMR: δ 7.34–6.99 (9H, m), 5.84–5.49 (2H, m), 4.82 (3H, br), 4.39 and 3.97 (2H, each m), 3.94 (2H, s), 3.19 (2H, s), 3.37–2.22 (10H, m), 1.83 (2H, m).

Example 2(xx)

11 α, 15-dihydroxy-9-oxo-20-methoxy-3,7-dithiaprost-13E-enoic acid

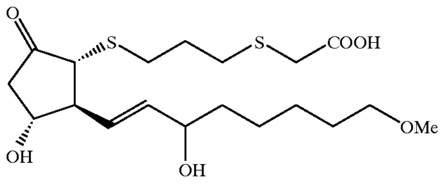

less polar: TLC: Rf 0.31,0.23 (ethyl acetate:acetic acid=50:1); NMR: δ 5.81 (1H, dd, J=15.4, 5.4 Hz), 5.67 (1H, dd, J=15.4, 7.6 Hz), 4.54–3.70 (5H, br m), 3.42 (2H, t, J=6.2 Hz), 3.35 (3H, s), 3.21 (2H, s), 3.07–2.25 (8H, m), 1.97–1.81 (2H, m), 1.70–1.25 (8H, m).

more polar: TLC: Rf 0.23, 0.13 (ethyl acetate:acetic acid=50:1); NMR: δ 6.00–5.20 (5H, br m), 4.47–4.05 (2H, m), 3.42 (2H, t, J=6.4 Hz), 3.35 (3H, s), 3.22 (2H, s), 3.05–2.20 (8H, m), 1.97–1.81 (2H, m), 1.75–1.25 (8H, m).

Example 2(yy)

11 α, 15-dihydroxy-9-oxo-16-(3-methyl-4-hydroxyphenyl)-17,18,19,20-tetranor-3,7-dithiaprost-13E-enoic acid

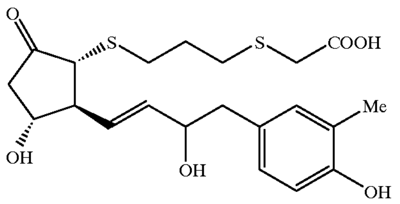

less polar: TLC: Rf 0.41, 0.33 (ethyl acetate:acetic acid=50:1); NMR ($CD_3OD$): δ 6.88 (2H, m), 6.64 (1H, d, J, 8.2 Hz), 5.82–5.42 (2H, m), 4.23 and 4.03 (2H, each m), 3.22 (2H, s), 3.56–2.17 (10H, m), 2.15 (3H, s), 1.86 (2H, m).

more polar: TLC: Rf 0.39, 0.22 (ethyl acetate:acetic acid=50:1); NMR ($CD_3OD$): δ 6.88 (2H, m), 6.64 (1H, d, J=8.0 Hz), 5.72 (1H, dd, J=15, 6.2 Hz), 5.56 (1H, dd, J=15, 7.8 Hz), 4.37–3.95 (2H, m), 3.22 (2H, s), 3.48–2.13 (10H, m), 2.15 (3H, s), 1.82 (2H, m).

Example 2(zz)

11 α, 15-dihydroxy-9-oxo-16-(3-cyanophenyl)-17,18,19, 20-tetranor-3,7-dithiaprost-13E-enoic acid

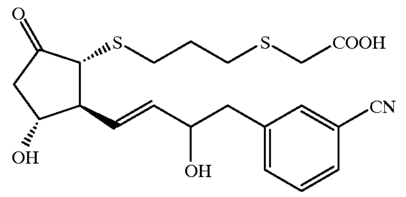

less polar: TLC: Rf 0.50, 0.44 (ethyl acetate:acetic acid=20:1); NMR ($CDCl_3$+$CD_3OD$): δ 7.6–7.4 (m, 4H), 5.9–5.55 (m, 2H), 4.45–4.3 and 4.1–3.95 (m, 2H), 3.22 (s, 2H), 3.45–3.4 and 3.0–2.3 (m, 13H), 2.0–1.8 (m, 2H).

more polar: TLC: Rf 0.47, 0.33 (ethyl acetate:acetic acid=20:1); NMR ($CDCl_3$+$CD_3OD$): δ 7.6–7.4 (m, 4H), 5.85–5.5 (m, 2H), 4.45–4.3 and 4.1–3.95 (m, 2H), 3.22 (s, 2H), 3.4–3.35 and 3.0–2.2 (m, 13H), 2.0–1.8 (m, 2H).

Example 2(aaa)

11 α, 15-dihydroxy-9-oxo-16-(3-propyloxymethylphenyl)-17,18,19,20-tetranor-3,7-dithiaprost-13E-enoic acid

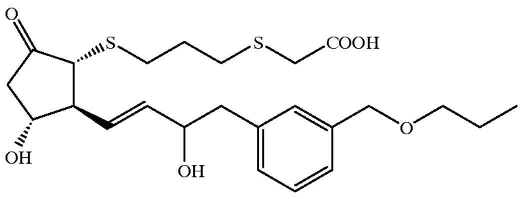

less polar: TLC: Rf 0.56, 0.46 (ethyl acetate:acetic acid=50:1); NMR: δ 7.37–7.09 (4H, m), 5.84–5.32 (2H, m), 5.20 (3H, br), 4.47 (2H, s), 4.57–3.76 (2H, m), 3.50 and 3.48 (2H, each t, J=7.0 Hz and 6.8 Hz), 3.21 (2H, s), 3.38–2.12 (10H, m), 1.86 (2H, m), 1.64 (2H, m), 0.94 (3H, t, J=7.4 Hz).

more polar: TLC: Rf 0.54, 0.44 (ethyl acetate:acetic acid=50:1); NMR: δ 7.37–7.10 (4H, m), 5.89–5.48 (2H, m), 4.58–3.87 (2H, m), 4.48 (2H, s), 4.42 (3H, br), 3.49 and 3.48 (2H, each t, J=6.7 Hz and 6.7 Hz), 3.21 (2H, s), 3.38–2.14 (10H, m), 1.87 (2H, m), 1.65 (2H, m), 0.94 (3H, 1, J=7.5 Hz).

Example 2(bbb)

11 α, 15-dihydroxy-9-oxo-16-(3-phenylethynylphenyl)-17, 18,19,20-tetranor-3,7-dithiaprost-13E-enoic acid

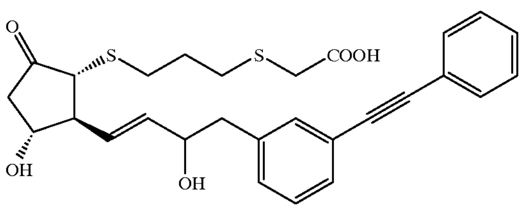

less polar TLC: Rf 0.41, 0.37 (ethyl acetate:acetic acid=50:1); NMR: δ 7.64–7.12 (9H, m), 5.90–5.45 (2H, m), 4.56–3.62 (5H, m), 3.44–2.10 (12H, m), 1.97–1.74 (2H, m).

more polar TLC: Rf 0.37, 0.33 (ethyl acetate:acetic acid=50:1); NMR: δ 7.60–7.11 (9H, m), 5.89–5.67 (1H, m), 5.57

(1H, dd, J=15.4 Hz, 8.0 Hz), 4.94–4.30 (4H, m), 4.12–3.93 (1H, m), 3.42–2.12 (12H, m), 1.95–1.72 (2H, m).

Example 2(ccc)

11 α, 15-dihydroxy-9-oxo-16-(4-hydroxyphenyl)-17,18,19,20-tetranor-3,7-dithiaprost-13E-enoic acid

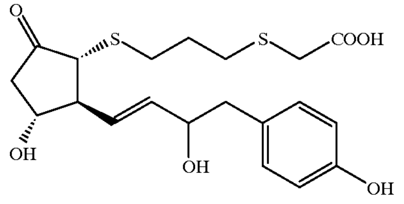

less polar: TLC: Rf 0.53, 0.44 (ethyl acetate:acetic acid=50:1); NMR ($CD_3OD$): δ 7.05 (2H, d, J=8.0 Hz), 6.70 (2H, d, J=8.0 Hz), 5.82–5.45 (2H, m), 5.00–4.70 (4H, br), 4.38–4.19 (1H, m), 4.10–3.98 (1H, m), 3.48–2.13 (10H, m), 3.22 (2H, s), 1.90–1.78 (2H, m).

more polar: TLC: Rf 0.50, 0.35 (ethyl acetate:acetic acid=50:1); NMR ($CD_3OD$): δ 7.05 (2H, d, J=8.4 Hz), 6.69 (2H, d, J=8.4 Hz), 5.73 (1H, dd, J=15.4, 6.2 Hz), 5.56 (1H, dd, J=15.4, 7.4 Hz), 4.95–4.80 (4H, br), 4.38–4.19 (1H, m), 4.10–3.98 (1H, m), 3.48–2.15 (10H, m), 3.22 (2H, s), 1.91–1.87 (2H, m).

Example 2(ddd)

11 α, 15-dihydroxy-9-oxo-16-(3-hydroxyphenyl)-17,18,19,20-tetranor-3,7-dithiaprost-13E-enoic acid

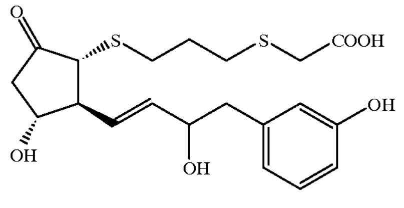

less polar: TLC: Rf 0.32, 0.26 (ethyl acetate:acetic acid=50:1); NMR ($CD_3OD$): δ 7.16–7.00 (1H, m), 6.80–6.56 (3H, m), 5.86–5.44 (2H, m), 4.40–3.96 (2H, m), 3.57–2.07 (12H, m), 1.98–1.74 (2H, m).

more polar: TLC: Rf 0.30, 0.24 (ethyl acetate:acetic acid=50:1); NMR ($CD_3OD$): δ 7.15–7.02 (1H, m), 6.78–6.56 (3H, m), 5.74 (1H, dd, J=15.4 Hz, 15.8 Hz), 5.67–5.51 (1H, m), 4.38–4.23 (1H, m), 4.11–3.95 (1H, m), 3.50–2.06 (12H, m), 1.97–1.72 (2H, m).

Example 2(eee)

11 α, 15-dihydroxy-9-oxo-16-(3-vinylphenyl)-17,18,19,20-tetranor-3,7-dithiaprost-13E-enoic acid

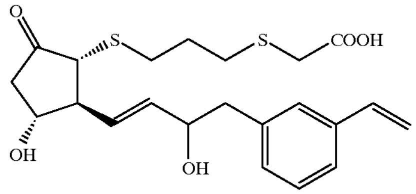

less polar: TLC: Rf 0.34, 0.27 (ethyl acetate:acetic acid=50:1); NMR: δ 7.38–7.04 (4H, m), 6.69 (1H, dd, J=17.6 Hz, 10.6 Hz), 5.90–5.44 (3H, m), 5.26 (1H, d, J=10.6 Hz), 5.20–4.52 (3H, br), 4.52–3.86 (2H, m), 3.40–2.08 (12H, m), 1.98–1.76 (2H, m).

more polar: TLC: Rf 0.29, 0.19 (ethyl acetate:acetic acid=50:1); NMR: δ 7.37–7.05 (4H, m), 6.68 (1H, dd, J=17.8 Hz, 10.8 Hz), 5.92–5.50 (3H, m), 5.44–4.70 (4H, m), 4.54–3.92 (2H, m), 3.40–2.10 (12H, m), 1.96–1.74 (2H, m).

Example 2(fff)

11 α, 15-dihydroxy-9-oxo-16-[3-(3-methoxypropyl)phenyl]-17,18,19,20-tetranor-3,7-dithiaprost-13E-enoic acid

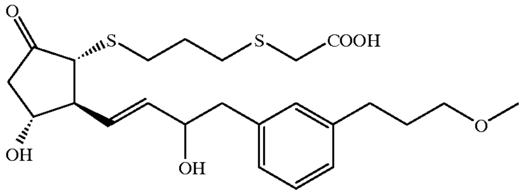

less polar: TLC: Rf 0.31, 0.27 (ethyl acetate:acetic acid=50:1); NMR: δ 7.30–6.98 (4H, m), 5.88–5.46 (2H, m), 5.20–4.50 (3H, br), 4.50–3.88 (2H, m), 3.42 (2H, t, J=6.2 Hz), 3.35 (3H, s), 3.21 (2H, s), 3.01–2.10 (12H, m), 1.99–1.78 (4H, m).

more polar: TLC: Rf 0.27, 0.21 (ethyl acetate:acetic acid=50:1); NMR: δ 7.30–6.97 (4H, m), 5.90–5.68 (1H, m), 5.60 (1H, dd, J=15.4 Hz, 8.0 Hz), 5.50–5.00 (3H, br), 4.52–4.28 (1H, m), 4.13–3.94 (1H, m), 3.42 (2H, t, J=6.4 Hz), 3.35 (3H, s), 3.21 (2H, s), 3.04–2.13 (12H, m), 1.99–1.76 (4H, m).

Example 2(ggg)

11 α, 15-dihydroxy-9-oxo-16-(3-methoxy-5-methoxymethylphenyl)-17,18,19,20-tetranor-3,7-dithiaprost-13E-enoic acid

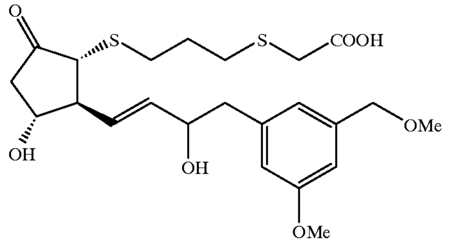

less polar: TLC: Rf 0.45, 0.37 (ethyl acetate:acetic acid=20:1); NMR: δ 6.76 (3H, m), 5.85–5.36 (2H, m), 4.46 (3H, br), 4.42 and 4.40 (2H, each s), 4.49–3.82 (2H, m), 3.81 (3H, s), 3.43 and 3.42 (3H, each s), 3.21 (2H, s), 3.38–2.12 (10H, m), 1.87 (2H, m).

more polar: TLC: Rf 0.39, 0.26 (ethyl acetate:acetic acid=20:1); NMR: δ 6.75 (3H, m), 5.88–5.49 (2H, m), 4.94 (3H, br), 4.57–3.91 (2H, m), 4.41 (2H, s), 3.80 (3H, s), 3.42 and 3.41 (3H, each s), 3.21 (2H, s), 3.38–2.14 (10H, m), 1.86 (2H, m).

Example 2(hhh)

11 α, 15-dihydroxy-9-oxo-16-[3-(2-methoxypropyl)phenyl]-17,18,19,20-tetranor-3,7-dithiaprost-13E-enoic acid

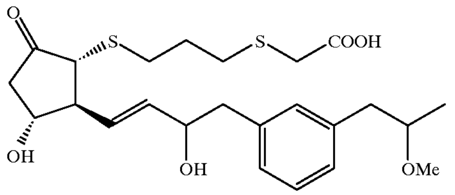

less polar: TLC: Rf 0.31, 0.21 (ethyl acetate:acetic acid=50:1); NMR: δ 7.27–7.03 (4H, m), 5.83–5.43 (2H, m), 5.20–4.40 (3H, br), 4.50–4.40 (1H, m), 4.02–3.90 (1H, m), 3.70–3.55 (1H, m), 3.32 (3H, s), 3.21 (2H, s), 2.98–2.30 (12H, m), 2.00–1.80 (2H, m), 1.17–1.13 (3H, m).

more polar: TLC: Rf 0.28, 0.14 (ethyl acetate:acetic acid=50:1); NMR: δ 7.25–7.00 (4H, m), 5.88–5.55 (2H, m), 5.40–4.50 (3H, br), 4.50–4.35 (1H m), 4.10–3.96 (1H, m), 3.70–3.50 (1H, m), 3.32 (3H, s), 3.21 (2H, s), 3.00–2.30 (12H, m), 1.95–1.80 (2H, m), 1.17–1.13 (3H, m).

Example 2(iii)

11 α, 15-dihydroxy-9-oxo-16-(3-methoxymethylphenyl)-17,18,19,20-tetranor-3,7-dithiaprostanoic acid

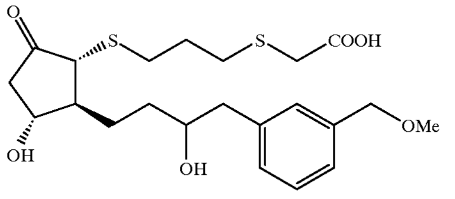

more polar: TLC: Rf 0.28 (ethyl acetate:acetic acid=19:1); NMR: δ 7.35–7.1 (m, 4H), 5.3–4.7 (br, 3H), 4.43 (s, 2H), 4.35–4.2 and 4.15–4.0 (m, 1H), 4.0–3.9 (m, 1H), 3.42 (s, 3H), 3.22 (s, 2H), 3.4–3.3 and 3.1–2.4 (m, 9H), 2.3–2.1 (m, 1H), 2.05–1.65 (m, 6H).

Example 2(jjj)

11 α, 15-dihydroxy-9-oxo-16-(3-methyl-5-methoxymethylphenyl)-17,18,19,20-tetranor-3,7-dithiaprost-13E-enoic acid

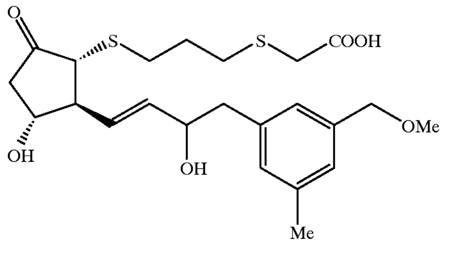

less polar: TLC: Rf 0.40, 0.31 (ethyl acetate:acetic acid=50:1); NMR: δ 7.02–6.92 (3H, br s), 5.81–5.10 (5H, m), 4.43–4.32 (3H, m), 3.94–3.80 (1H, m), 3.41 (3H, s), 3.21 (2H, s), 3.00–2.20 (10H, m), 2.33 (3H, s), 1.95–1.79 (2H, m).

more polar: TLC: Rf 0.23,0.14 (ethyl acetate:acetic acid=50:1); NMR: δ 7.02–6.92 (3H, br s), 5.81 (1H, dd, J=15.8, 5.8 Hz), 5.56 (1H, dd, J=15.8, 7.8 Hz), 5.50–4.70 (3H, br), 4.53–4.28 (1H, m), 4.40 (2H, s), 4.03–3.91 (1H, m), 3.41 (3H, s), 3.21 (2H, s), 2.99–2.30 (10H, m), 2.33 (3H, s), 1.93–1.79 (2H, m).

Example 2(kkk)

11 α, 15-dihydroxy-9-oxo-19-methoxy-20-nor-3,7-dithiaprost-13E-enoic acid

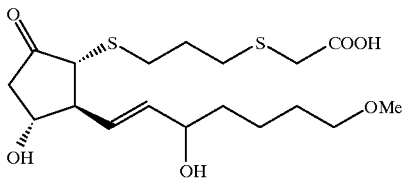

less polar: TLC: Rf 0.30, 0.25 (ethyl acetate:acetic acid=10:1); NMR: δ 5.87–5.58 (2H, m), 4.52–4.04 (2H, m), 4.04–3.60 (3H, br), 3.48–3.38(2H, m), 3.34 (3H, s), 3.21 (2H, s), 3.08–2.18 (8H, m), 2.00–1.80 (2H, m), 1.80–1.30 (6H, m).

more polar: TLC: Rf 0.25, 0.16 (ethyl acetate:acetic acid=10:1); NMR: δ 5.86–5.57 (2H, m), 5.57–5.20 (3H, br), 4.54–4.02 (2H, m), 3.54–3.38 (2H, m), 3.35 (3H, s), 3.30–2.16 (10H, m), 1.98–1.78 (2H, m), 1.73–1.34 (6H, m).

Example 2(lll)

11 α, 15-dihydroxy-9-oxo-16-[3-(2-propenyloxymethyl)phenyl]-17,18,19,20-tetranor-3,7-dithiaprost-13E-enoic acid

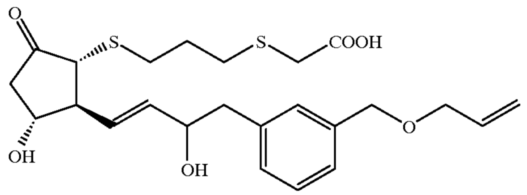

less polar: TLC: Rf 0.40, 0.34 (ethyl acetate:acetic acid=50:1); NMR: δ 7.35–7.10 (4H, m), 6.08–5.10 (8H, m), 4.60–3.72 (6H, m), 3.40–2.10 (12H, m), 1.96–1.74 (2H, m).

more polar: TLC: Rf 0.32, 0.21 (ethyl acetate:acetic acid=50:1); NMR: δ 7.37–7.09 (4H, m), 6.07–5.18 (8H, m), 4.62–3.86 (6H, m), 3.40–2.12 (12H, m), 1.96–1.74 (2H, m).

Example 2(mmm)

11 α, 15-dihydroxy-9-oxo-16-(3-cyclohexyloxymethylphenyl)-17,18,19,20-tetranor-3,7-dithiaprost-13E-enoic acid

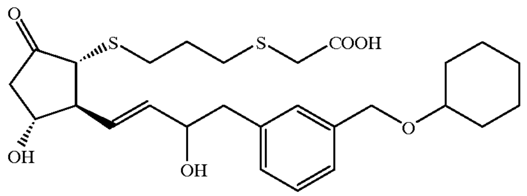

less polar: TLC: Rf 0.59, 0.53 (ethyl acetate:acetic acid=50:1); NMR: δ 7.35–7.08 (4H, m), 5.86–5.28 (2H, m), 4.60–3.70 (7H, m), 3.50–3.28 (1H, m), 3.20 (2H, s), 3.15–2.10 (10H, m), 2.10–1.04 (12H, m).

more polar: TLC: Rf 0.40 (ethyl acetate:acetic acid=50:1); NMR: δ 7.34–7.08 (4H, m), 5.90–5.46 (2H, m), 5.10–4.60

(3H, br), 4.60–3.70 (4H, m), 3.50–3.28 (1H, m), 3.20 (2H, s), 3.14–2.24 (10H, m), 2.10–1.10 (12H, m).

Example 2(nnn)

11 α, 15-dihydroxy-9-oxo-16-methyl-16-(3-methoxymethylphenyl)-17,18,19,20-tetranor-3,7-dithiaprost-13E-enoic acid

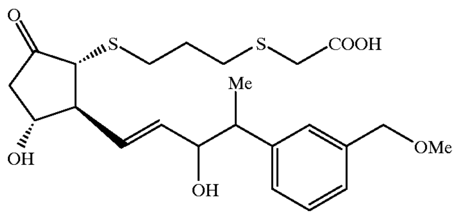

less polar: TLC: Rf 0.38, 0.31 (ethyl acetate:acetic acid=50:1); NMR: δ 7.35–7.13 (4H, m), 5.66–5.46 (1H, m), 5.28 (1H, dd, J=15.4, 8.6 Hz), 5.00–4.30 (3H, br), 4.42 (2H, s), 4.27–3.97 (1H, m), 3.80–3.55 (1H, m), 3.44 (3H, s), 3.21 (2H, s), 2.95–1.77 (11H, m), 1.41 (3H, d, J=7.0 Hz).

more polar: TLC: Rf 0.36, 0.22 (ethyl acetate:acetic acid=50:1); NMR: δ 7.35–7.13 (4H, m), 6.00–5.20 (5H, m), 4.50–3.72 (4H, m), 3.42 (3H, s), 3.20 (2H, s), 3.02–2.23 (9H, m), 1.92–1.78 (2H, m), 1.37–1.25 (3H, m).

Example 2(ooo)

11 α, 15-dihydroxy-9-oxo-16-[3-(2-ethyoxyethyl)phenyl]-17,18,19,20-tetranor-3,7-dithiaprost-13E-enoic acid

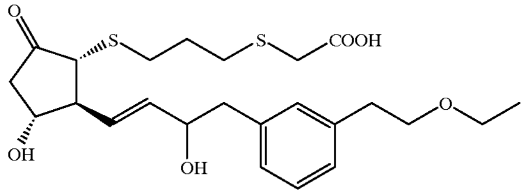

less polar: TLC: Rf 0.38, 0.27 (ethyl acetate:acetic acid=50:1); NMR: δ 7.27–7.03 (4H, m), 5.90–5.49 (2H, m), 5.20–4.40 (3H, br), 4.48–4.38 (1H, m), 4.30–3.85 (1H, m), 3.68 (2H, t, J=7.0 Hz), 3.53 (2H, q, J=7.0 Hz), 3.21 (2H, s), 2.97–2.15 (12H, m), 1.97–1.80 (2H, m), 1.20 (3H, t, J=7.0 Hz).

more polar: TLC: Rf 0.35, 0.22 (ethyl acetate:acetic acid=50:1); NMR: δ 7.27–7.03 (4H, m), 5.86–5.54 (2H, m), 5.20–4.40 (3H, br), 4.50–3.93 (2H, m), 3.67 (2H, t, J=7.0 Hz), 3.53 (2H, q, J=7.0 Hz), 3.21 (2H, s), 3.00–2.20 (12H, m), 1.97–1.80 (2H, m), 1.19 (3H, t, J=7.0 Hz).

Example 2(ppp)

11 α, 15-dihydroxy-9-oxo-16-(3-propyl-4-hydroxyphenyl)-17,18,19,20-tetranor-3,7-dithiaprost-13E-enoic acid

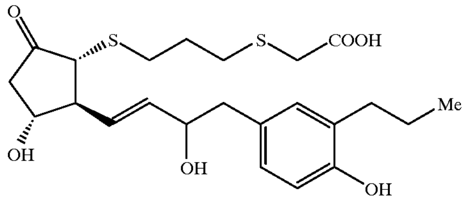

less polar: TLC: Rf 0.42, 0.34 (ethyl acetate:acetic acid=50:1); NMR ($CD_3OD$): δ 6.95–6.81 (2H, m), 6.65 (1H, d, J=8.0 Hz), 5.82–5.43 (2H, m), 4.30–3.98 (2H, m), 3.55–2.18 (12H, m), 3.22 (2H, s), 1.95–1.79 (2H, m), 1.70–1.48 (2H, m), 0.94 (3H, t, J=7.2 Hz).

more polar: TLC: Rf 0.37, 0.24 (ethyl acetate:acetic acid=50:1); NMR ($CD_3OD$): δ 6.93–6.81 (2H, m), 6.65 (1H, d, J=8.2 Hz), 5.73 (1H, dd, J=15.4, 6.2 Hz), 5.57 (1H, dd, J=15.4, 7.4 Hz), 4.36–3.97 (2H, m), 3.47–2.10 (12H, m), 3.22 (2H, s), 1.88–1.77 (2H, m), 1.68–1.49 (2H, m), 0.94 (3H, t, J=7.4 Hz).

Example 2(qqq)

11 α, 15-dihydroxy-9-oxo-16-(3-methoxymethyl-4-hydroxyphenyl)-17,18,19,20-tetranor-3,7-dithiaprost-13E-enoic acid

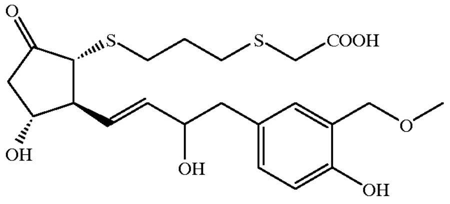

less polar: TLC: Rf 0.31, 0.24 (ethyl acetate:acetic acid=50:1); NMR ($CD_3OD$): δ 7.12–7.06 (m, 1H), 6.99–6.96 (m, 1H), 6.71 (d, J=8.1 Hz, 1H), 5.81–5.46 (m, 2H), 4.47 (s, 2H), 4.30–4.18 (m, 1H), 4.14–3.92 (m, 1H), 3.53–3.48 & 3.07–3.01 (m, 1H), 3.39 (s, 3H), 3.22 (s, 2H), 3.00–2.09 (m, 9H), 1.93–1.76 (m, 2H).

more polar: TLC: Rf 0.26, 0.20 (ethyl acetate:acetic acid=50:1); NMR ($CD_3OD$): δ 7.09 (s, 1H), 7.04–6.93 (m, 1H), 6.70 (d, J=8.1 Hz, 1H), 5.72 (dd, J=15.3 Hz, 6.3 Hz, 1H), 5.56 (dd, J=15.3 Hz, 8.1 Hz, 1H), 4.46 (s, 2H), 4.35–4.19 (m, 1H), 4.15–3.96 (m, 1H), 3.48–3.43 & 3.08–3.02 (m, 1H), 3.38 (s, 3H), 3.21 (s, 2H), 3.01–2.10 (m, 9H), 1.93–1.73 (m, 2H).

Formulation Example

The following components were admixed in conventional method and dried. Microcrystalline cellulose was added to the mixture to obtain the total weight of 10 g. The resulting mixture was mixed sufficiently to make it homogenous and then tabletted in conventional manner to give 100 tablets each containing 30 μg of the active ingredient.

| | |
|---|---|
| A solution of 11α,15α-dihydroxy-9-oxo-16-(3-methoxymethylphenyl)-17,18,19,20-tetranor-3,7-dithiaprost-13-enoic acid (3 mg) in ethanol | 10 ml |
| magnesium stearate | 100 mg |
| silicon dioxide | 20 mg |
| talc | 10 mg |
| carboxymethylcellulose calcium | 200 mg |
| microcrystalline cellulose | 5.0 g |

We claim:

1. A 3,7-dithiaprostanoic acid derivative of the formula (I)

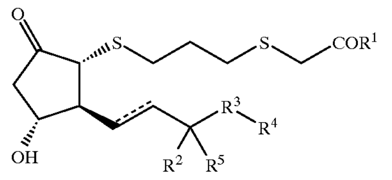

(I)

wherein $R^1$ is hydroxy, C1~6 alkyloxy or a group of the formula:

$NR^6R^7$ (in which $R^6$ and $R^7$ are independently hydrogen or C1~6 alkyl);

$R^2$ is hydrogen or hydroxy;

$R^3$ is single bond or C1~6 alkylene;

$R^4$ is (i) C1~8 alkyl, C2~8 alkenyl or C2~8 alkynyl substituted by one to three substituent(s) selected from the group consisting of C1~6 alkyloxy and halogen atom, (ii) phenyloxy or C3~7 cycloalkyloxy, (iii) furyl, furyloxy, thienyl, thienyloxy, naphthyl, naphthyloxy, phthalanyl or phthalanyloxy, (iv) phenyl, phenyloxy, C3~7 cycloalkyl or C3~7 cycloalkyloxy substituted by one to three substituent(s) selected from the group consisting of the following groups:

C1~6 alkyl,
C2~6 alkenyl,
C2~6 alkynyl,
C1~6 alkyloxy,
C1~6 alkyloxy-C1~6 alkyl,
C1~6 alkyloxy-C1~6 alkyloxy,
C2~6 alkenyloxy-C1~6 alkyl,
C1~6 alkyl substituted by 1 to 3 of hydroxy,
C1~6 alkyl substituted by 1 to 3 of halogen atom(s),
C1~6 alkylthio,
C1~6 alkylthio-C1~6 alkyl,
C1~6 alkylthio-C1~6 alkyloxy,
C2~6 alkenylthio-C1~6 alkyl,
C1~6 alkylsulfonyl,
halogen,
trihalomethyl,
cyano,
nitro,
amino,
hydroxy,
C3~7 cycloalkyl,
C3~7 cycloalkyloxy,
C3~7 cycloalkyl-C1~6 alkyl,
C3~7 cycloalkyloxy-C1~6 alkyl,
phenyl,
phenyloxy,
phenyl-C1~6 alkyl,
phenyl-C2~6 alkenyl,
phenyl-C2~6 alkynyl,
phenyloxy-C1~6 alkyl,
phenyloxy-C2~6 alkenyl,
phenyloxy-C2~6 alkynyl,
furyl,
furyloxy,
furyl-C1~6 alkyl,
furyloxy-C1~6 alkyl,
thienyl,
thienyloxy,
thienyl-C1~6 alkyl and
thienyloxy-C1~6 alkyl (the above mentioned phenyl, furyl, thienyl or cycloalkyl may be substituted by one to three substituent(s) selected from the group consisting of C1~6 alkyl, C1~6 alkyloxy, C1~6 alkyloxy-C1~6 alkyl, nitro, halogen, trihalomethyl, amino and hydroxy); or, (v) furyl, furyloxy, thienyl, thienyloxy, naphthyl, naphthyloxy, phthalanyl or phthalanyloxy substituted by one to three substituent(s) selected from the group consisting of the following groups:

C1~6 alkyl,
C2~6 alkenyl,
C2~6 alkynyl,
C1~6 alkyloxy,
C1~6 alkyloxy-C1~6 alkyl,
C1~6 alkyloxy-C1~6 alkyloxy,
C2~6 alkenyloxy-C1~6 alkyl,
C1~6 alkyl substituted by 1 to 3 of hydroxy,
C1~6 alkyl substituted by 1 to 3 of halogen atom(s),
C1~6 alkylthio,
C1~6 alkylthio-C1~6 alkyl,
C1~6 alkylthio-C1~6 alkyloxy,
C2~6 alkenylthio-C1~6 alkyl,
C1~6 alkylsulfonyl,
halogen,
trihalomethyl,
cyano,
nitro,
amino,
hydroxy,
C3~7 cycloalkyl,
C3~7 cycloalkyloxy,
C3~7 cycloalkyl-C1~6 alkyl,
C3~7 cycloalkyloxy-C1~6 alkyl,
phenyl,
phenyloxy,
phenyl-C1~6 alkyl,
phenyl-C2~6 alkenyl,
phenyl-C2~6 alkynyl,
phenyloxy-C1~6 alkyl,
phenyloxy-C2~6 alkenyl,
phenyloxy-C2~6 alkynyl,
furyl,
furyloxy,
furyl-C1~6 alkyl,
furyloxy-C1~6 alkyl,
thienyl,
thienyloxy,
thienyl-C1~6 alkyl and
thienyloxy-C1~6 alkyl (the above mentioned phenyl, furyl, thienyl or cycloalkyl may be substituted by one to three substituent(s) selected from the group consisting of C1~6 alkyl, C1~6 alkyloxy, C1~6 alkyloxy-C1~6 alkyl, nitro, halogen, trihalomethyl, amino and hydroxy);

$R^5$ is hydrogen or C1~6 alkyl; and
the symbol

is double bond or single bond;

the formula including the 8-epi equilibrium compound; with the proviso that when $R^2$ is hydrogen, C1~6 alkylene represented by $R^3$ may be substituted by a hydroxy group;

or a non-toxic salt thereof or a cyclodextrin clathrate thereof.

2. A compound according to claim 1, in which $R^1$ is hydroxy.

3. A compound according to claim 1, in which $R^1$ is C1~6 alkyloxy.

4. A compound according to claim 1, in which $R^1$ is a group of the formula:

$NR^6R^7$ in which $R^6$ and $R^7$ are independently hydrogen or C1~6 alkyl.

5. A compound according to claim 1, in which $R^4$ is (i) C1~8 alkyl, C2~8 alkenyl or C2~8 alkynyl substituted by one to three substituent(s) selected from the group consisting of C1~6 alkyloxy and halogen atom.

6. A compound according to claim 1, in which $R^4$ is (ii) phenyloxy or C3~7 cycloalkyloxy.

7. A compound according to claim 1, in which $R^4$ is (iii) furyl, furyloxy, thienyl, thienyloxy, naphthyl, naphthyloxy, phthalanyl or phthalanyloxy.

8. A compound according to claim 1, in which $R^4$ is (iv) phenyl, phenyloxy, C3~7 cycloalkyl or C3~7 cycloalkyloxy substituted by one to three substituent(s) selected from the group consisting of the following groups:

C1~6 alkyl,
C2~6 alkenyl,
C2~6 alkynyl,
C1~6 alkyloxy,
C1~6 alkyloxy-C1~6 alkyl,
C1~6 alkyloxy-C1~6 alkyloxy,
C2~6 alkenyloxy-C1~6 alkyl,
C1~6 alkyl substituted by 1 to 3 of hydroxy,
C1~6 alkyl substituted by 1 to 3 of halogen atom(s),
C1~6 alkylthio,
C1~6 alkylthio-C1~6 alkyl,
C1~6 alkylthio-C1~6 alkyloxy,
C2~6 alkenylthio-C1~6 alkyl,
C1~6 alkylsulfonyl,
halogen,
trihalomethyl,
cyano,
nitro,
amino,
hydroxy,
C3~7 cycloalkyl,
C3~7 cycloalkyloxy,
C3~7 cycloalkyl-C1~6 alkyl,
C3~7 cycloalkyloxy-C1~6 alkyl,
phenyl,
phenyloxy,
phenyl-C1~6 alkyl,
phenyl-C2~6 alkenyl,
phenyl-C2~6 alkynyl,
phenyloxy-C1~6 alkyl,
phenyloxy-C2~6 alkenyl,
phenyloxy-C2~6 alkynyl,
furyl,
furyloxy,
furyl-C1~6 alkyl,
furyloxy-C1~6 alkyl,
thienyl,
thienyloxy,
thienyl-C1~6 alkyl and
thienyloxy-C1~6 alkyl (the above mentioned phenyl, furyl, thienyl or cycloalkyl may be substituted by one to three substituent(s) selected from the group consisting of C1~6 alkyl, C1~6 alkyloxy, C1~6 alkyloxy-C1~6 alkyl, nitro, halogen, trihalomethyl, amino and hydroxy).

9. A compound according to claim 1, in which $R^4$ is (v) furyl, furyloxy, thienyl, thienyloxy, naphthyl, naphthyloxy, phthalanyl or phthalanyloxy substituted by one to three substituent(s) selected from the group consisting of the following groups:

C1~6 alkyl,
C2~6 alkenyl,
C2~6 alkynyl,
C1~6 alkyloxy,
C1~6 alkyloxy-C1~6 alkyl,
C1~6 alkyloxy-C1~6 alkyloxy,
C2~6 alkenyloxy-C1~6 alkyl,
C1~6 alkyl substituted by 1 to 3 of hydroxy,
C1~6 alkyl substituted by 1 to 3 of halogen atom(s),
C1~6 alkylthio,
C1~6 alkylthio-C1~6 alkyl,
C1~6 alkylthio-C1~6 alkyloxy,
C2~6 alkenylthio-C1~6 alkyl,
C1~6 alkylsulfonyl,
halogen,
trihalomethyl,
cyano,
nitro,
amino,
hydroxy,
C3~7 cycloalkyl,
C3~7 cycloalkyloxy,
C3~7 cycloalkyl-C1~6 alkyl,
C3~7 cycloalkyloxy-C1~6 alkyl,
phenyl,
phenyloxy,
phenyl-C1~6 alkyl,
phenyl-C2~6 alkenyl,
phenyl-C2~6 alkynyl,
phenyloxy-C1~6 alkyl,
phenyloxy-C2~6 alkenyl,
phenyloxy-C2~6 alkynyl,
furyl,
furyloxy, furyl-C1~6 alkyl, furyloxy-C1~6 alkyl, thienyl, thienyloxy, thienyl-C1~6 alkyl and thienyloxy-C1~6 alkyl (the above mentioned phenyl, furyl, thienyl or cycloalkyl may be substituted by one to three substituent(s) selected from the group consisting of C1~6 alkyl, C1~6 alkyloxy, C1~6 alkyloxy-C1~6 alkyl, nitro, halogen, trihalomethyl, amino and hydroxy).

10. A compound according to claim 1, which is selected from the group consisting of (1) 11 α, 15-dihydroxy-9-oxo-20-methoxy-3,7-dithiaprost-13E-enoic acid and (2) 11 α, 15-dihydroxy-9-oxo-19-methoxy-20-nor-3,7-dithiaprost-13E-enoic acid and methyl ester thereof.

11. A compound according to claim 1, which is selected from the group consisting of 11 α, 15 α-dihydroxy-9-oxo-16-phenyloxy-17,18,19,20-tetranor-3,7-dithiaprost-13E-enoic acid and methyl ester thereof.

12. A compound according to claim 1, which is selected from the group consisting of (1) 11 α, 15-dihydroxy-9-oxo-16-(3-thienyl)-17,18,19,20-tetranor-3,7-dithiaprost-13E-enoic acid, (2) 11 α, 15-dihydroxy-9-oxo-16-(2-thienyl)-17,18,19,20-tetranor-3,7-dithiaprost-13E-enoic acid, (3) 11 α, 15-dihydroxy-9-oxo-16-(2-naphthyl)-17,18,19,20-tetranor-3,7-dithiaprost-13E-enoic acid and (4) 11 α, 15-dihydroxy-9-oxo-16-(5-phthalanyl)-17,18,19,20-tetranor-3,7-dithiaprost-13E-enoic acid and methyl ester thereof.

13. A compound according to claim 1, which is selected from the group consisting of (1) 11 α, 15 α-dihydroxy-9-oxo-16-(3-methoxymethylphenyl)-17,18,19,20-tetranor-3,7-dithiaprost-13E-enoic acid, (2) 11 α, 15-dihydroxy-9-oxo-16-(4-methylphenyl)-17,18,19,20-tetranor-3,7-dithiaprost-13E-enoic acid, (3) 11 α, 15-dihydroxy-9-oxo-16-(4-chlorophenyl)-17,18,19,20-tetranor-3,7-dithiaprost-13E-enoic acid, (4) 11 α, 15-dihydroxy-9-oxo-16-(4-methoxyphenyl)-17,18,19,20-tetranor-3,7-dithiaprost-13E-enoic acid, (5) 11 α, 15-dihydroxy-9-oxo-16-(2-methylphenyl)-17,18,19,20-tetranor-3,7-dithiaprost-13E-enoic acid, (6) 11 α, 15-dihydroxy-9-oxo-16-(3-methoxyphenyl)-17,18,19,20-tetranor-3,7-dithiaprost-13E-enoic acid, (7) 11 α, 15-dihydroxy-9-oxo-16-(3-chlorophenyl)-17,18,19,20-tetranor-3,7-dithiaprost-13E-enoic acid, (8) 11 α, 15-dihydroxy-9-oxo-16-(3-methylphenyl)-17,18,19,20-tetranor-3,7-dithiaprost-13E-enoic acid, (9) 11 α, 15-dihydroxy-9-oxo-16-(2-methoxyphenyl)-17,18,19,20-tetranor-3,7-dithiaprost-13E-enoic acid,

(10) 11 α, 15-dihydroxy-9-oxo-16-(4-methoxy-3-chlorophenyl)-17,18,19,20-tetranor-3,7-dithiaprost-13E-enoic acid,

(11) 11 α, 15-dihydroxy-9-oxo-16-(3-trifluoromethylphenyl)-17,18,19,20-tetranor-3,7-dithiaprost-13E-enoic acid,

(12) 11 α, 15-dihydroxy-9-oxo-16-(4-methoxymethylphenyl)-17,18,19,20-tetranor-3,7-dithiaprost-13E-enoic acid,

(13) 11 α, 15-dihydroxy-9-oxo-16-(3,4-dichlorophenyl)-17,18,19,20-tetranor-3,7-dithiaprost-13E-enoic acid,

(14) 11 α, 15-dihydroxy-9-oxo-16-(4-methylthiophenyl)-17,18,19,20-tetranor-3,7-dithiaprost-13E-enoic acid,

(15) 11 α, 15-dihydroxy-9-oxo-16-(3-methylthiophenyl)-17,18,19,20-tetranor-3,7-dithiaprost-13E-enoic acid,

(16) 11 α, 15-dihydroxy-9-oxo-16-(biphenyl-3-yl)-17,18,19,20-tetranor-3,7-dithiaprost-13E-enoic acid,

(17) 11 α, 15-dihydroxy-9-oxo-16-(3-ethylphenyl)-17,18,19,20-tetranor-3,7-dithiaprost-13E-enoic acid,

(18) 11 α, 15-dihydroxy-9-oxo-16-(3,5-dimethylphenyl)-17,18,19,20-tetranor-3,7-dithiaprost-13E-enoic acid,

(19) 11 α, 15-dihydroxy-9-oxo-16-(3-methoxymethylphenyl)-17,18,19,20-tetranor-3,7-dithiaprost-13E-enoic acid,

(20) 11 α, 15-dihydroxy-9-oxo-16-(2-methoxy-3-methylphenyl)-17,18,19,20-tetranor-3,7-dithiaprost-13E-enoic acid,

(21) 11 α, 15-dihydroxy-9-oxo-16-(4-mesylphenyl)-17,18,19,20-tetranor-3,7-dithiaprost-13E-enoic acid,

(22) 11 α, 15-dihydroxy-9-oxo-16-(2,3-dimethylphenyl)-17,18,19,20-tetranor-3,7-dithiaprost-13E-enoic acid,

(23) 11 α, 15-dihydroxy-9-oxo-16-(4-ethoxyphenyl)-17,18,19,20-tetranor-3,7-dithiaprost-13E-enoic acid,

(24) 11 α, 15-dihydroxy-9-oxo-16-(3-ethoxyphenyl)-17,18,19,20-tetranor-3,7-dithiaprost-13E-enoic acid,

(25) 11 α, 15-dihydroxy-9-oxo-16-(3,4-dimethoxyphenyl)-17,18,19,20-tetranor-3,7-dithiaprost-13E-enoic acid, (26)11 α, 15-dihydroxy-9-oxo-16-(3-methyl-4-methoxyphenyl)-17,18,19,20-tetranor-3,7-dithiaprost-13E-enoic acid,

(27) 11 α, 15-dihydroxy-9-oxo-16-(3-isopropylphenyl)-17,18,19,20-tetranor-3,7-dithiaprost-13E-enoic acid,

(28) 11 α, 15-dihydroxy-9-oxo-16-(2,5-dimethylphenyl)-17,18,19,20-tetranor-3,7-dithiaprost-13E-enoic acid,

(29) 11 α, 15-dihydroxy-9-oxo-16-(2-methoxy-5-chlorophenyl)-17,18,19,20-tetranor-3,7-dithiaprost-13E-enoic acid,

(30) 11 α, 15-dihydroxy-9-oxo-16-(5-methoxy-3-methylphenyl)-17,18,19,20-tetranor-3,7-dithiaprost-13E-enoic acid,

(31) 11 α, 15-dihydroxy-9-oxo-16-(3-propylphenyl)-17,18,19,20-tetranor-3,7-dithiaprost-13E-enoic acid,

(32) 11 α, 15-dihydroxy-9-oxo-16-[3-(2-furyl)phenyl]-17,18,19,20-tetranor-3,7-dithiaprost-13E-enoic acid,

(33) 11 α, 15-dihydroxy-9-oxo-16-(3-mesylphenyl)-17,18,19,20-tetranor-3,7-dithiaprost-13E-enoic acid,

(34) 11 α, 15-dihydroxy-9-oxo-16-(3-ethoxymethylphenyl)-17,18,19,20-tetranor-3,7-dithiaprost-13E-enoic acid,

(35) 11 α, 15-dihydroxy-9-oxo-16-(3-methylthiomethylphenyl)-17,18,19,20-tetranor-3,7-dithiaprost-13E-enoic acid,

(36) 11 α, 15-dihydroxy-9-oxo-16-(3-hydroxymethylphenyl)-17,18,19,20-tetranor-3,7-dithiaprost-13E-enoic acid,

(37) 11 α, 15-dihydroxy-9-oxo-16-[3-(2-methoxyethyl)phenyl]-17,18,19,20-tetranor-3,7-dithiaprost-13E-enoic acid,

(38) 11 α, 15-dihydroxy-9-oxo-16-[3-(1-methoxyethyl)phenyl]-17,18,19,20-tetranor-3,7-dithiaprost-13E-enoic acid,

(39) 11 α, 15-dihydroxy-9-oxo-16-(3-phenoxymethylphenyl)-17,18,19,20-tetranor-3,7-dithiaprost-13E-enoic acid,

(40) 11 α, 15-dihydroxy-9-oxo-16-(3-isopropyloxymethylphenyl)-17,18,19,20-tetranor-3,7-dithiaprost-13E-enoic acid,

(41) 11 α, 15-dihydroxy-9-oxo-16-[3-(2-fluoroethyl)phenyl]-17,18,19,20-tetranor-3,7-dithiaprost-13E-enoic acid,

(42) 11 α, 15-dihydroxy-9-oxo-16-[3-(2-thienyl)phenyl]-17,18,19,20-tetranor-3,7-dithiaprost-13E-enoic acid,

(43) 11 α, 15-dihydroxy-9-oxo-16-[3-(1-propynyl)phenyl]-17,18,19,20-tetranor-3,7-dithiaprost-13E-enoic acid,

(44) 11 α, 15-dihydroxy-9-oxo-16-(3-benzylphenyl)-17,18,19,20-tetranor-3,7-dithiaprost-13E-enoic acid, (45) 11 α, 15-dihydroxy-9-oxo-16-(3-methyl-4-hydroxyphenyl)-17,18,19,20-tetranor-3,7-dithiaprost-13E-enoic acid,

(46) 11 α, 15-dihydroxy-9-oxo-16-(3-cyanophenyl)-17,18,19,20-tetranor-3,7-dithiaprost-13E-enoic acid,

(47) 11 α, 15-dihydroxy-9-oxo-16-(3-propyloxymethylphenyl)-17,18,19,20-tetranor-3,7-dithiaprost-13E-enoic acid,

(48) 11 α, 15-dihydroxy-9-oxo-16-(3-phenylethynylphenyl)-17,18,19,20-tetranor-3,7-dithiaprost-13E-enoic acid,

(49) 11 α, 15-dihydroxy-9-oxo-16-(4-hydroxyphenyl)-17,18,19,20-tetranor-3,7-dithiaprost-13E-enoic acid,

(50) 11 α, 15-dihydroxy-9-oxo-16-(3-hydroxyphenyl)-17,18,19,20-tetranor-3,7-dithiaprost-13E-enoic acid,

(51) 11 α, 15-dihydroxy-9-oxo-16-(3-vinylphenyl)-17,18,19,20-tetranor-3,7-dithiaprost-13E-enoic acid,

(52) 11 α, 15-dihydroxy-9-oxo-16-[3-(3-methoxypropyl)phenyl]-17,18,19,20-tetranor-3,7-dithiaprost-13E-enoic acid,

(53) 11 α, 15-dihydroxy-9-oxo-16-(3-methoxy-5-methoxymethylphenyl)-17,18,19,20-tetranor-3,7-dithiaprost-13E-enoic acid,

(54) 11 α, 15-dihydroxy-9-oxo-16-[3-(2-methoxypropyl)phenyl]-17,18,19,20-tetranor-3,7-dithiaprost-13E-enoic acid,

(55) 11 α, 15-dihydroxy-9-oxo-16-(3-methoxymethylphenyl)-17,18,19,20-tetranor-3,7-dithiaprostanoic acid,

(56) 11 α, 15-dihydroxy-9-oxo-16-(3-methyl-5-methoxymethylphenyl)-17,18,19,20-tetranor-3,7-dithiaprost-13E-enoic acid,

(57) 11 α, 15-dihydroxy-9-oxo-16-[3-(2-propenyloxymethyl)phenyl]-17,18,19,20-tetranor-3,7-dithiaprost-13E-enoic acid,

(58) 11 α, 15-dihydroxy-9-oxo-16-(3-cyclohexyloxymethylphenyl)-17,18,19,20-tetranor-3,7-dithiaprost-13E-enoic acid,

(59) 11 α, 15-dihydroxy-9-oxo-16-methyl-16-(3-methoxymethylphenyl)-17,18,19,20-tetranor-3,7-dithiaprost-13E-enoic acid,

(60) 11 α, 15-dihydroxy-9-oxo-16-[3-(2-ethoxyethyl)phenyl]-17,18,19,20-tetranor-3,7-dithiaprost-13E-enoic acid,

(61) 11 α, 15-dihydroxy-9-oxo-16-(3-propyl-4-hydroxyphenyl)-17,18,19,20-tetranor-3,7-dithiaprost-13E-enoic acid and

(62) 11 α, 15-dihydroxy-9-oxo-16-(3-methoxymethyl-4-hydroxyphenyl)-17,18,19,20-tetranor-3,7-dithiaprost-13E-enoic acid and methyl ester thereof.

14. A compound according to claim 1, which is selected from the group consisting of 11 α, 15-dihydroxy-9-oxo-16-(5-methoxymethylthiophen-2-yl)-17,18,19,20-tetranor-3,7-dithiaprost-13E-enoic acid and methyl ester thereof.

15. A pharmaceutical composition comprising a 3,7-dithiaprostanoic acid derivative of the formula (I) depicted in claim 1, or a non-toxic salt thereof or a cyclodextrin clathrate thereof as an active ingredient.

16. A method of the prevention and/or treatment of immunological diseases, asthma, abnormal bone formation, neuronal cell death, liver damage, nephritis, hypertension, myocardiac ischemia or sleeping disorder which comprises administering to a patient an effective amount of a 3,7-dithiaprostanoic acid derivative of the formula (I) depicted in claim 1, or a non-toxic salt thereof or a cyclodextrin clathrate thereof, as an active ingredient.

* * * * *